(12) United States Patent
Lewi et al.

(10) Patent No.: US 7,585,861 B2
(45) Date of Patent: Sep. 8, 2009

(54) HIV INHIBITING 1,2,4-TRIAZINES

(75) Inventors: Paulus Joannes Lewi, Turnhout (BE); Paul Adriaan Jan Janssen, Vosselaar (BE); Frank Jozef Herwig Arts, legal representative, Brasschaat (BE); Marc René de Jonge, Tilburg (NL); Lucien Maria Henricus Koymans, Retie (BE); Hendrik Maarten Vinkers, Antwerp (BE); Frederik Frans Desiré Daeyaert, Beerse (BE); Jan Heeres, Vosselaar (BE); Ruben Gerardus George Leenders, Nijmegen (NL); Georges Joseph Cornelius Hoornaert, Kessel-Lo (BE); Amuri Kilonda, Kessel-Lo (BE); Donald William Ludovici, Quakertown, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 10/544,584

(22) PCT Filed: Feb. 5, 2004

(86) PCT No.: PCT/EP2004/050084

§ 371 (c)(1),
(2), (4) Date: Oct. 31, 2006

(87) PCT Pub. No.: WO2004/074266

PCT Pub. Date: Sep. 2, 2004

(65) Prior Publication Data

US 2007/0037811 A1     Feb. 15, 2007

(30) Foreign Application Priority Data

Feb. 7, 2003     (EP) .................... PCT/EP03/01289

(51) Int. Cl.
*C07D 253/075*     (2006.01)
*A61K 31/53*       (2006.01)
*A61P 31/18*       (2006.01)
*C07D 403/12*      (2006.01)
*C07D 403/14*      (2006.01)

(52) U.S. Cl. .................... 514/242; 544/182
(58) Field of Classification Search ................ 544/182; 514/242

See application file for complete search history.

(56) References Cited

U.S. PATENT DOCUMENTS 3,459,731 A    8/1969 Gramera et al.

FOREIGN PATENT DOCUMENTS

| EP | 1270560 A1 | 1/2003 |
|---|---|---|
| EP | 09455443 B9 | 2/2003 |
| EP | 1002795 B1 | 3/2003 |
| EP | 0834507 B1 | 5/2004 |
| WO | WO 97/18839 A1 | 5/1997 |
| WO | WO 99/50250 A1 | 10/1999 |
| WO | WO 99/50258 A1 | 10/1999 |
| WO | WO 00/27828 A2 | 5/2000 |
| WO | WO 01/85700 A2 | 11/2001 |
| WO | WO 02/078708 A1 | 10/2002 |
| WO | WO 03/016306 A1 | 2/2003 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Barlow et al., "Heterocyclic Polyfluoro-compounds. Part 39. Preparation and Some Nucleophilic Substitution Reactions of Trifluoro—1,2,4-triazine.", J. Chem. Soc., 1982, vol. 5, pp. 1251-1254.
Cai et al., "Chemistry of 1,2,4-triazines. VIII. Oxidation of Ethyl 3-Methylthio-5hydroxy-1,2,4-triazine-6-carboxylate and ethyl N2-[5'-3'-methylthio-6'-ethoxycarbonyl)-1',2',4'-triazinyl]-3-methlthio-5-oxo-1',2',4'-triazine-6-carboxylate and the substitution reactions of the oxidized products.", Huaxue Xuebao (1987), 45(2), pp. 185-190. English Abstract only.
Koyanagi et al., "Selective Cytotoxicity of AIDS Virus Infection Towards HTLV-I-Transformed Cell Lines.", Int. J. Cancer, 1985, vol. 36, pp. 445-451.
Kumar et al, "Synthesis of Dicationic Diarylpyridines as Neucleic-acid Binding Agents.", European Journal of Medicinal Chemistry, Editions Scientifique Elsevier, Paris, France, vol. 30, No. 2, 1995, pp. 99-106.
Nogradi, M., "Dimethyl-B-Cyclodextrin.", Drugs of The Future, 1984, vol. 9, No. 8, pp. 577-578.
International Search Report, International Application No. PCT/EP2004/050084, Date of Mailing of International Search Report Jul. 29, 2004.
Barlow, M. et al., J. Chem. Soc., Perkin Transactions 1. Organic and Bio-organic Chemistry (1972-1999), 5, 1251-1254.
Meng-Shen, C. et al., Acta Chimica Sinica, (1987), 45(2), 185-190 (see English Abstract provided).

* cited by examiner

*Primary Examiner*—Venkataraman Balasubramanian

(57) ABSTRACT

The present invention relates to HIV replication inhibitors of formula (I) as defined in the specification their use as a medicine, their processes for preparation and pharmaceutical compositions comprising them.

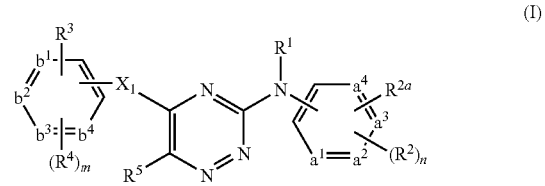

(I)

19 Claims, No Drawings

HIV INHIBITING 1,2,4-TRIAZINES

CROSS REFERENCE TO RELATED APPLICATIONS

This application is the national stage of Application No. PCT/EP2004/050084 filed Feb. 5, 2004, which application claims priority from PCT/EP03/01289, filed Feb. 7, 2003.

The present invention is concerned with 1,2,4-triazine derivatives having HIV (Human Immunodeficiency Virus) replication inhibiting properties. The invention further relates to methods for their preparation and pharmaceutical compositions comprising them. The invention also relates to the use of said compounds for the manufacture of a medicament for the prevention or the treatment of HIV infection.

Compounds structurally related to the present compounds are disclosed in the prior art. In Huaxue Xuebao (1987), 45(2), 185-190, and J. Chem. Soc., Perkin Transactions 1. Organic and Bio-organic Chemistry (1972-1999) (1982), 5, 1251-1254 the synthesis of 1,2,4-triazine derivatives is disclosed.

The compounds of the invention differ from prior art compounds in structure, pharmacological activity and/or pharmacological potency.

The compounds of the invention are highly active to inhibit the replication of Human Immunodeficiency Virus (HIV), and in particular they are highly active to inhibit the replication of mutant strains, in particular drug or multidrug resistant HIV strains, i.e. strains which have become resistant to one or more art-known NNRTI drug(s) (Non Nucleoside Reverse Transcriptase Inhibitor drugs).

The present invention concerns a compound of formula

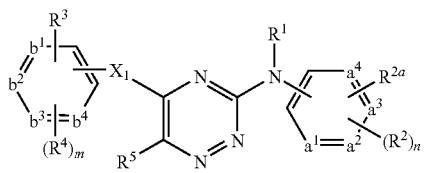

(I)

a N-oxide, a pharmaceutically acceptable addition salt, a quaternary amine or a stereochemically isomeric form thereof, wherein -$a^1$=$a^2$-$a^3$=$a^4$- represents a bivalent radical of formula
—CH═CH—CH═CH— (a-1);
—N═CH—CH═CH— (a-2);
—N═CH—N═CH— (a-3);
—N═CH—CH═N— (a-4);
—N═N—CH═CH— (a-5);

-$b^1$=$b^2$-$b^3$=$b^4$- represents a bivalent radical of formula
—CH═CH—CH═CH— (b-1);
—N═CH—CH═CH— (b-2);
—N═CH—N═CH— (b-3);
—N═CH—CH═N— (b-4);
—N═N—CH═CH— (b-5);

n is 0, 1, 2, 3 and in case -$a^1$=$a^2$-$a^3$=$a^4$- is (a-1), then n may also be 4;

m is 0, 1, 2, 3 and in case -$b^1$=$b^2$-$b^3$=$b^4$- is (b-1), then m may also be 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

each $R^2$ independently is hydroxy; halo; $C_{1-6}$alkyl optionally substituted with one or more substituents each independently selected from halo, cyano or —C(═O)$R^6$; $C_{3-7}$cycloalkyl; $C_{2-6}$alkenyl optionally substituted with one or more substituents each independently selected from halo, cyano or —C(═O)$R^6$; $C_{2-6}$alkynyl optionally substituted with one or more substituents each independently selected from halo, cyano or —C(═O)$R^6$; $C_{1-6}$alkyloxycarbonyl; carboxyl; cyano; nitro; amino; mono- or di($C_{1-6}$alkyl)amino; polyhalomethyl; polyhalomethylthio; —S(═O)$_p$$R^6$; —NH—S(═O)$_p$$R^6$; —C(═O)$R^6$; —NHC(═O)H; —C(═O)NHNH$_2$; NHC(═O)$R^6$; C(═NH)$R^6$;

$R^{2a}$ is cyano; aminocarbonyl; amino; $C_{1-6}$alkyl; halo; $C_{1-6}$alkyloxy wherein $C_{1-6}$alkyl may optionally be substituted with cyano; NH$R^{13}$; N$R^{13}R^{14}$; —C(═O)—NH$R^{13}$; —C(═O)—N$R^{13}R^{14}$; —C(═O)—$R^{15}$; —CH═N—NH—C(═O)—$R^{16}$; $C_{1-6}$alkyl substituted with one or more substituents each independently selected from halo, cyano, N$R^9R^{10}$, —C(═O)—N$R^9R^{10}$, —C(═O)—$C_{1-6}$alkyl or $R^7$; $C_{1-6}$alkyl substituted with hydroxy and a second substituent selected from halo, cyano, N$R^9R^{10}$, —C(═O)—N$R^9R^{10}$, —C(═O)—$C_{1-6}$alkyl or $R^7$; $C_{1-6}$alkyloxy$C_{1-6}$alkyl optionally substituted with one or more substituents each independently selected from halo, cyano, N$R^9R^{10}$, —C(═O)—N$R^9R^{10}$, —C(═O)—$C_{1-6}$alkyl or $R^7$; $C_{2-6}$alkenyl substituted with one or more substituents each independently selected from halo, cyano, N$R^9R^{10}$, —C(═O)—N$R^9R^{10}$, —C(═O)—$C_{1-6}$alkyl or $R^7$; $C_{2-6}$alkynyl substituted with one or more substituents each independently selected from halo, cyano, N$R^9R^{10}$, —C(═O)—N$R^9R^{10}$, —C(═O)—$C_{1-6}$alkyl or $R^7$; —C(═N—O—$R^8$)—$C_{1-4}$alkyl; $R^7$ or —$X_3$—$R^7$;

$X_1$ is —N$R^1$—, —NH—NH—, —N═N—, —O—, —C(═O)—, $C_{1-4}$alkanediyl, —CHOH—, —S—, —S(═O)$_p$—, —$X_2$—$C_{1-4}$alkanediyl- or —$C_{1-4}$alkanediyl-$X_2$—;

$X_2$ is —N$R^1$—, —NH—NH—, —N═N—, —O—, —C(═O)—, —CHOH—, —S—, —S(═O)$_p$—;

$R^3$ is cyano; aminocarbonyl; amino; $C_{1-6}$alkyl; halo; $C_{1-6}$alkyloxy wherein $C_{1-6}$alkyl may optionally be substituted with cyano; NH$R^{13}$; N$R^{13}R^{14}$; —C(═O)—NH$R^{13}$; —C(═O)—N$R^{13}R^{14}$; —C(═O)—$R^{15}$; —CH═N—NH—C(═O)—$R^{16}$; $C_{1-6}$alkyl substituted with one or more substituents each independently selected from halo, cyano, N$R^9R^{10}$, —C(═O)—N$R^9R^{10}$, —C(═O)—$C_{1-6}$alkyl or $R^7$; $C_{1-6}$alkyl substituted with hydroxy and a second substituent selected from halo, cyano, N$R^9R^{10}$, —C(═O)—N$R^9R^{10}$, —C(═O)—$C_{1-6}$alkyl or $R^7$; $C_{1-6}$alkyloxy$C_{1-6}$alkyl optionally substituted with one or more substituents each independently selected from halo, cyano, N$R^9R^{10}$, —C(═O)—N$R^9R^{10}$, —C(═O)—$C_{1-6}$alkyl or $R^7$; $C_{2-6}$alkenyl substituted with one or more substituents each independently selected from halo, cyano, N$R^9R^{10}$, —C(═O)—N$R^9R^{10}$, —C(═O)—$C_{1-6}$alkyl or $R^7$; $C_{2-6}$alkynyl substituted with one or more substituents each independently selected from halo, cyano, N$R^9R^{10}$, —C(═O)—N$R^9R^{10}$, —C(═O)—$C_{1-6}$alkyl or $R^7$; —C(═N—O—$R^8$)—$C_{1-4}$alkyl; $R^7$ or —$X_3$—$R^7$;

$X_3$ is —N$R^1$—, —NH—NH—, —N═N—, —O—, —C(═O)—, —S—, —S(═O)$_p$—, —$X_2$—$C_{1-4}$alkanediyl-, —$C_{1-4}$alkanediyl-$X_{2a}$—, —$C_{1-4}$alkanediyl-$X_{2b}$—$C_{1-4}$alkanediyl, —C(═N—O$R^8$)—$C_{1-4}$alkanediyl-;

with $X_{2a}$ being —NH—NH—, —N═N—, —O—, —C(═O)—, —S—, —S(═O)$_p$—; and with $X_{2b}$ being —NH—NH—, —N═N—, —C(═O)—, —S—, —S(═O)$_p$—;

R⁴ is halo; hydroxy; C₁₋₆alkyl optionally substituted with one or more substituents each independently selected from halo, cyano or —C(=O)R⁶; C₂₋₆alkenyl optionally substituted with one or more substituents each independently selected from halo, cyano or —C(=O)R⁶; C₂₋₆alkynyl optionally substituted with one or more substituents each independently selected from halo, cyano or —C(=O)R⁶; C₃₋₇cycloalkyl; C₁₋₆alkyloxy; cyano; nitro; polyhaloC₁₋₆alkyl; polyhaloC₁₋₆alkyloxy; aminocarbonyl; mono- or di(C₁₋₄alkyl)aminocarbonyl; C₁₋₆alkyloxycarbonyl; C₁₋₆alkylcarbonyl; formyl; amino; mono- or di(C₁₋₄alkyl)amino or R⁷;

R⁵ is hydrogen; halo; aminocarbonyl; mono- or di(C₁₋₄alkyl)aminocarbonyl; amino; C₁₋₆alkyloxycarbonyl; C₁₋₆alkyloxycarbonylamino; polyhaloC₁₋₆alkyl; C₁₋₆alkyl optionally substituted with cyano, hydroxy, halo, C₁₋₆alkyloxy, C₁₋₆alkylthio or S(=O)ₚ—C₁₋₆alkyl; C₂₋₆alkenyl optionally substituted with cyano, hydroxy, halo, C₁₋₆alkyloxy, C₁₋₆alkylthio or S(=O)ₚ—C₁₋₆alkyl; C₂₋₆alkynyl optionally substituted with cyano, hydroxy, halo, C₁₋₆alkyloxy, C₁₋₆alkylthio or S(=O)ₚ—C₁₋₆alkyl;

R⁶ is C₁₋₄alkyl, amino, mono- or di(C₁₋₄alkyl)amino or polyhaloC₁₋₄alkyl;

R⁷ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C₁₋₆alkyl, hydroxyC₁₋₆alkyl, aminoC₁₋₆alkyl, mono or di(C₁₋₆alkyl)aminoC₁₋₆alkyl, formyl, C₁₋₆alkylcarbonyl, C₃₋₇cycloalkyl, C₁₋₆alkyloxy, C₁₋₆alkyloxycarbonyl, C₁₋₆alkylthio, cyano, nitro, polyhaloC₁₋₆alkyl, polyhaloC₁₋₆alkyloxy, aminocarbonyl, —CH(=N—O—R⁸), R⁷ᵃ, —X₃—R⁷ᵃ or R⁷ᵃ—C₁₋₄alkyl;

R⁷ᵃ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C₁₋₆alkyl, hydroxyC₁₋₆alkyl, aminoC₁₋₆alkyl, mono or di(C₁₋₆alkyl)aminoC₁₋₆alkyl, formyl, C₁₋₆alkylcarbonyl, C₃₋₇cycloalkyl, C₁₋₆alkyloxy, C₁₋₆alkyloxycarbonyl, C₁₋₆alkylthio, cyano, nitro, polyhaloC₁₋₆alkyl, polyhaloC₁₋₆alkyloxy, aminocarbonyl, —CH(=N—O—R⁸);

R⁸ is hydrogen, C₁₋₄alkyl, aryl or arylC₁₋₄alkyl;

R⁹ and R¹⁰ each independently are hydrogen; hydroxy; C₁₋₆alkyl; C₁₋₆alkyloxy; C₁₋₆alkylcarbonyl; C₁₋₆alkyloxycarbonyl; amino; mono- or di(C₁₋₄alkyl)amino; mono- or di(C₁₋₄alkyl)aminocarbonyl; —CH(=NR¹¹) or R⁷, wherein each of the aforementioned C₁₋₆alkyl groups may optionally and each individually be substituted with one or two substituents each independently selected from hydroxy, C₁₋₆alkyloxy, hydroxyC₁₋₆alkyloxy, carboxyl, C₁₋₆alkyloxycarbonyl, cyano, amino, imino, mono- or di(C₁₋₄alkyl)amino, polyhalomethyl, polyhalomethyloxy, polyhalomethylthio, —S(=O)ₚR⁶, —NH—S(=O)ₚR⁶, —C(=O)R⁶, —NHC(=O)H, —C(=O)NHNH₂, —NHC(=O)R⁶, —C(=NH)R⁶, R⁷; or R⁹ and R¹⁰ may be taken together to form a bivalent or trivalent radical of formula
—CH₂—CH₂—CH₂—CH₂— (d-1)
—CH₂—CH₂—CH₂—CH₂—CH₂— (d-2)
—CH₂—CH₂—O—CH₂—CH₂— (d-3)
—CH₂—CH₂—S—CH₂—CH₂— (d-4)
—CH₂—CH₂—NR¹²—CH₂—CH₂— (d-5)
—CH₂—CH=CH—CH₂— (d-6)
=CH—CH=CH—CH=CH— (d-7)

R¹¹ is cyano; C₁₋₄alkyl optionally substituted with C₁₋₄alkyloxy, cyano, amino, mono- or di(C₁₋₄alkyl)amino or aminocarbonyl; C₁₋₄alkylcarbonyl; C₁₋₄alkyloxycarbonyl; aminocarbonyl; mono- or di(C₁₋₄alkyl)aminocarbonyl;

R¹² is hydrogen or C₁₋₄alkyl;

R¹³ and R¹⁴ each independently are C₁₋₆alkyl optionally substituted with cyano or aminocarbonyl, C₂₋₆alkenyl optionally substituted with cyano or aminocarbonyl, C₂₋₆alkynyl optionally substituted with cyano or aminocarbonyl;

R¹⁵ is C₁₋₆alkyl substituted with cyano or aminocarbonyl;

R¹⁶ is C₁₋₆alkyl optionally substituted with cyano or aminocarbonyl, or R⁷;

p is 1 or 2;

aryl is phenyl or phenyl substituted with one, two, three, four or five substituents each independently selected from halo, hydroxy, mercapto, C₁₋₆alkyl, hydroxyC₁₋₆alkyl, aminoC₁₋₆alkyl, mono or di(C₁₋₆alkyl)aminoC₁₋₆alkyl, C₁₋₆alkylcarbonyl, C₃₋₇cycloalkyl, C₁₋₆alkyloxy, C₁₋₆alkyloxycarbonyl, C₁₋₆alkylthio, cyano, nitro, polyhaloC₁₋₆alkyl, polyhaloC₁₋₆alkyloxy, aminocarbonyl, R⁷ or —X₃—R⁷ provided the following compounds
1,2,4-triazine-6-carboxylic acid, 3,5-bis[(4-methylphenyl)amino]-, ethyl ester,
1,2,4-triazine-6-carboxylic acid, 3,5-bis[(4-nitrophenyl)amino]-, ethyl ester;
N,N'-bis(4-chlorophenyl)-6-fluoro-1,2,4-triazine-3,5-diamine;
are not included.

The present invention also relates to the use of a compound for the manufacture of a medicament for the treatment or prevention of HIV infection, wherein the compound has the formula

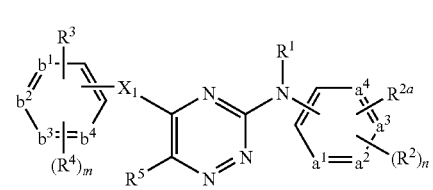

(I)

a N-oxide, a pharmaceutically acceptable addition salt, a quaternary amine or a stereochemically isomeric form thereof, wherein -a¹=a²-a³=a⁴- represents a bivalent radical of formula
—CH=CH—CH=CH— (a-1);
—N=CH—CH=CH— (a-2);
—N=CH—N=CH— (a-3);
—N=CH—CH=N— (a-4);
—N=N—CH=CH— (a-5); p0 -b¹=b²-b³=b⁴- represents a bivalent radical of formula
—CH=CH—CH=CH— (b-1);
—N=CH—CH=CH— (b-2);
—N=CH—N=CH— (b-3);
—N=CH—CH=N— (b-4);
—N=N—CH=CH— (b-5);

n is 0, 1, 2, 3 and in case -a¹=a²-a³=a⁴— is (a-1), then n may also be 4;

m is 0, 1, 2, 3 and in case -b¹=b²-b³=b⁴— is (b-1), then m may also be 4;

R$^1$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy; C$_{1-6}$alkyloxyC$_{1-6}$alkylcarbonyl substituted with C$_{1-6}$alkyloxycarbonyl;

each R$^2$ independently is hydroxy; halo; C$_{1-6}$alkyl optionally substituted with one or more substituents each independently selected from halo, cyano or —C(=O)R$^6$; C$_{3-7}$Cycloalkyl; C$_{2-6}$alkenyl optionally substituted with one or more substituents each independently selected from halo, cyano or —C(=O)R$^6$; C$_{2-6}$alkynyl optionally substituted with one or more substituents each independently selected from halo, cyano or —C(=O)R$^6$; C$_{1-6}$alkyloxycarbonyl; carboxyl; cyano; nitro; amino; mono- or di(C$_{1-6}$alkyl)amino; polyhalomethyl; polyhalomethylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$;

R$^{2a}$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_1$ is —NR$^1$—, —NH—NH—, —N=N—, —O—, —C(=O)—, C$_{1-4}$alkanediyl, —CHOH—, —S—, —S(=O)$_p$—, —X$_2$—C$_{1-4}$alkanediyl- or —C$_{1-4}$alkanediyl-X$_2$—;

X$_2$ is —NR$^1$—, —NH—NH—, —N=N—, —O—, —C(=O)—, —CHOH—, —S—, —S(=O)$_p$—;

R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_3$ is —NR$^1$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, —C$_{1-4}$alkanediyl-X$_{2b}$—C$_{1-4}$alkanediyl, —C(=N—OR$^8$)—C$_{1-4}$alkanediyl-;

with X$_{2a}$ being —NH—NH—, —N=N—, —O—, —C(=O)—, —S—, —S(=O)$_p$—; and
with X$_{2b}$ being —NH—NH—, —N=N—, —C(=O)—, —S—, —S(=O)$_p$—;

R$^4$ is halo; hydroxy; C$_{1-6}$alkyl optionally substituted with one or more substituents each independently selected from halo, cyano or —C(=O)R$^6$; C$_{2-6}$alkenyl optionally substituted with one or more substituents each independently selected from halo, cyano or —C(=O)R$^6$; C$_{2-6}$alkynyl optionally substituted with one or more substituents each independently selected from halo, cyano or —C(=O)R$^6$; C$_{3-7}$cycloalkyl; C$_{1-6}$alkyloxy; cyano; nitro; polyhaloC$_{1-6}$alkyl; polyhaloC$_{1-6}$alkyloxy; aminocarbonyl; mono- or di(C$_{1-4}$alkyl)aminocarbonyl; C$_{1-6}$alkyloxycarbonyl; C$_{1-6}$alkylcarbonyl; formyl; amino; mono- or di(C$_{1-4}$alkyl)amino or R$^7$;

R$^5$ is hydrogen; halo; aminocarbonyl; mono- or di(C$_{1-4}$alkyl)aminocarbonyl; amino; C$_{1-6}$alkyloxycarbonyl; C$_{1-6}$alkyloxycarbonylamino; polyhaloC$_{1-6}$alkyl; C$_{1-6}$alkyl optionally substituted with cyano, hydroxy, halo, C$_{1-6}$alkyloxy, C$_{1-6}$alkylthio or S(=O)$_p$—C$_{1-6}$alkyl; C$_{2-6}$alkenyl optionally substituted with cyano, hydroxy, halo, C$_{1-6}$alkyloxy, C$_{1-6}$alkylthio or S(=O)$_p$—C$_{1-6}$alkyl; C$_{2-6}$alkynyl optionally substituted with cyano, hydroxy, halo, C$_{1-6}$alkyloxy, C$_{1-6}$alkylthio or S(=O)$_p$—C$_{1-6}$alkyl;

R$^6$ is C$_{1-4}$alkyl, amino, mono- or di(C$_{1-4}$alkyl)amino or polyhaloC$_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkyl;

R$^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$));

R$^8$ is hydrogen, C$_{1-4}$alkyl, aryl or arylC$_{1-4}$alkyl;

R$^9$ and R$^{10}$ each independently are hydrogen; hydroxy; C$_{1-6}$alkyl; C$_{1-6}$alkyloxy; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R⁶, —NHC(=O)H, —C(=O)NHNH₂, —NHC(=O)R⁶, —C(=NH)R⁶, R⁷; or R⁹ and R¹⁰ may be taken together to form a bivalent or trivalent radical of formula —CH₂—CH₂—CH₂—CH₂— (d-1)
—CH₂—CH₂—CH₂—CH₂—CH₂— (d-2)
—CH₂—CH₂—O—CH₂—CH₂— (d-3)
—CH₂—CH₂—S—CH₂—CH₂— (d-4)
—CH₂—CH₂—NR¹²—CH₂—CH₂— (d-5)
—CH₂—CH=CH—CH₂— (d-6)
=CH—CH=CH—CH=CH— (d-7)

R¹¹ is cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

R¹² is hydrogen or $C_{1-4}$alkyl;

R¹³ and R¹⁴ each independently are $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

R¹⁵ is $C_{1-6}$alkyl substituted with cyano or aminocarbonyl;

R¹⁶ is $C_{1-6}$alkyl optionally substituted with cyano or aminocarbonyl, or R⁷;

p is 1 or 2;

aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, R⁷ or —X₃—R⁷.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like.

Particular examples of monocyclic, bicyclic or tricyclic partially saturated carbocycles are cyclopropenyl, cyclobutenyl, cyclopentenyl, cyclohexenyl, cycloheptenyl, cyclo-octenyl, bicyclo[4,2,0]octenyl, cyclononenyl, cyclodecenyl, octahydronaphthalenyl, 1,2,3,4tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydioquinolinyl, octahydroindolyl and the like.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4benzodioxinyl, indolinyl and the like.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imnidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolo-triazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhalo$C_{1-4}$alkyl or polyhalo$C_{1-6}$alkyl, they may be the same or different.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (eg. $R^7$, $X_2$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartalic, 2-hydroxy-1,2,3-propanetricarboxylic, methanesulfonic, ethanesulfonic, benzenesulfonic, 4-methylbenzenesulfonic, cyclohexanesulfamic, 2-hydcoxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R— or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

Whenever used hereinbefore or hereinafter that substituents can be selected each independently out of a list of numerous definitions, such as for example for $R^9$ and $R^{10}$, all possible combinations are intended which are chemically possible or which lead to chemically stable molecules.

An interesting group of compounds are those compounds of formula (I) wherein -$a^1$=$a^2$-$a^3$=$b^4$- represents a bivalent radical of formula —CH=CH—CH=CH— (a-1).

Also an interesting group of compounds are those compounds of formula (I) having the formula

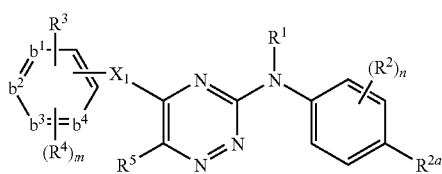

(I')

the N-oxides, the pharmaceutically acceptable addition salts, the quaternary amines or the stereochemically isomeric forms thereof, wherein -$b^1$=$b^2$-$b^3$=$b^4$-, $R^1$, $R^2$, $R^{2a}$, $R^3$, $R^4$, $R^5$, m, n and $X_1$ are as defined hereinabove.

Preferably $R^{2a}$ is cyano, aminocarbonyl, $C_{1-6}$alkyl optionally substituted with cyano or aminocarbonyl, $C_{2-6}$alkenyl optionally substituted with cyano or aminocarbonyl.

Another interesting group of compounds are those compounds of formula (I) or (I') wherein -$b^1$=$b^2$-$b^3$=$b^4$- represents a bivalent radical of formula (b-1).

Yet a further interesting group of compounds are those compounds of formula (I) having the formula

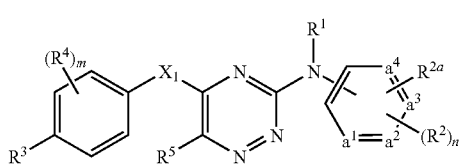

(I")

the N-oxides, the pharmaceutically acceptable addition salts, the quaternary amines or the stereochemically isomeric formns thereof, wherein -$a^1$=$a^2$-$a^3$=$a^4$-, $R^1$, $R^2$, $R^{2a}$, $R^3$, $R^4$, $R^5$, m, n and $X_1$ are as defined hereinabove.

Another interesting group of compounds are those compounds of formula (I) having the formula

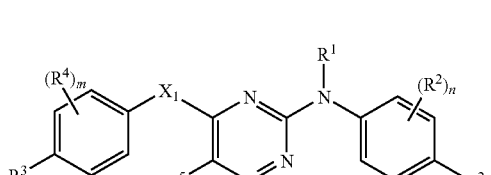

(I''')

the N-oxides, the pharmaceutically acceptable addition salts, the quaternary amines or the stereochemically isomeric forms thereof, wherein $R^1$, $R^2$, $R^{2a}$, $R^3$, $R^4$, $R^5$, m, n and $X_1$ are as defined hereinabove.

Preferably $R^{2a}$ is cyano, aminocarbonyl, $C_{1-6}$alkyl substituted with cyano or aminocarbonyl, $C_{2-6}$alkenyl substituted with cyano or aminocarbonyl.

An interesting embodiment are those compounds of formula (I), (I'), (I") or (I''') wherein at least one of m or n is other than 0.

Another interesting embodiment encompasses those compounds of formula (I) having the formula

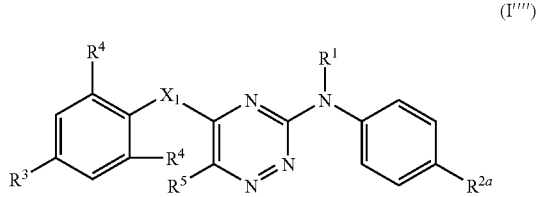

(I'''')

the N-oxides, the pharmaceutically acceptable addition salts, the quaternary amines or the stereochemically isomeric forms thereof, wherein $R^1$, $R^{2a}$, $R^3$, $R^4$, $R^5$ and $X_1$ are as defined hereinabove.

Also an interesting embodiment encompasses those compounds of formula (I) having the formula

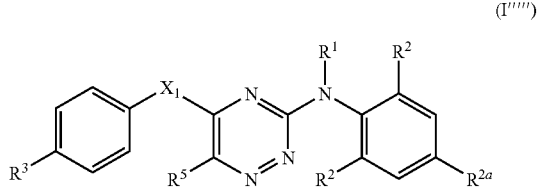

(I''''')

the N-oxides, the pharmaceutically acceptable addition salts, the quaternary amines or the stereochemically isomeric forms thereof, wherein $R^1$, $R^2$, $R^{2a}$, $R^3$, $R^5$ and $X_1$ are as defined hereinabove.

Also particular compounds are those compounds of formula (I), (I'), (I"), (I'''), (I'''') or (I''''') wherein one or wherever possible more of the following conditions apply:

a) m is 1, 2 or 3, in particular 2 or 3, more in particular 2, even more in particular m is 2 and said two $R^4$ substituents are placed in position 2 and 6 (ortho position) in respect of the $X_1$ moiety, b) m is 0;

c) m is 0 and $R^3$ is cyano or aminocarbonyl;

d) $X_1$ is —$NR^1$—, —O—, —C(=O)—, $C_{1-4}$alkanediyl, —CHOH—, —S(=O)$_p$— or S; in particular —$NR^1$—, O or S;

e) n is 0;

f) n is 1, 2 or 3, in particular 2 or 3, more in particular 2, even more in particular n is 2 and said two $R^2$ substituents are placed in position 2 and 6 (ortho position) in respect of the $NR^1$-linker;

g) n is 2 and $R^{2a}$ is cyano, aminocarbonyl, $C_{1-6}$alkyl optionally substituted with cyano or aminocarbonyl, or $C_{2-6}$alkenyl optionally substituted with cyano or aminocarbonyl;

h) $R^{2a}$ is cyano, aminocarbonyl, $C_{1-6}$alkyl substituted with cyano or aminocarbonyl, or $C_{2-6}$alkenyl substituted with cyano or aminocarbonyl; in particular cyano;

i) $R^3$ is $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$.

Another embodiment encompasses those compounds of formula (I), (I'), (I''), (I'''), (I'''') or (I''''') wherein $R^3$ is $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{2-6}$alkyl substituted with cyano or aminocarbonyl; $C_{1-6}$alkyl substituted with halo, $NR^9R^{10}$, —C(=O)—$NR^{9a}R^{10}$, —C(=O)—$C_{1-6}$alkyl or $R^7$; $C_{1-6}$alkyl substituted with two or more substituents each independently selected from halo, cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl or $R^7$; $C_{1-6}$allyloxy$C_{1-6}$alkyl optionally substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$; with $R^{9a}$ representing hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl, —CH(=$NR^{11}$) or $R^7$, wherein each of the aforementioned $C_{1-6}$alkyl groups in the definition of $R^{9a}$ may optionally and each individually be substituted with one or two substituents each independently selected from hydroxy, $C_{1-6}$allyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, $R^7$; $R^{9a}$ may also be taken together with $R^{10}$ to form a bivalent or trivalent radical of formula (d-1), (d-2), (d-3), (d-4), (d-5), (d-6) or (d-7) as defined hereinabove.

Also a preferred embodiment of the present invention encompasses those compounds of formula (I), (I'), (I''), (I'''), (I'''') or (I''''') wherein $R^1$ is hydrogen.

Also an interesting group of compounds are those compounds of formula (I), (I'), (I''), (I'''), (I'''') or (I''''') wherein one or more of the following restrictions apply:
a) $R^1$ is hydrogen;
b) $X_1$ is NH, S or O;
c) $R^5$ is hydrogen, $C_{1-6}$alkyl or halo;
d) $R^{2a}$ or $R^2$ is halo, cyano, aminocarbonyl, $C_{1-6}$alkyloxy, $C_{1-6}$alkyl, $C_{1-6}$alkyl substituted with cyano or $C_{2-6}$alkenyl substituted with cyano;
e) n is 0 or 2;
f) $R^3$ is $C_{1-6}$alkyl; cyano; aminocarbonyl; mono or di($C_{1-4}$alkyl)aminocarbonyl; $C_{1-6}$alkyl substituted with cyano or aminocarbonyl; $C_{2-6}$alkenyl substituted with cyano or aminocarbonyl or mono- or di($C_{1-4}$alkyl)aminocarbonyl or C(=O)$NR^9R^{10}$ wherein $R^9$ and $R^{10}$ are taken together; halo; $C_{1-6}$alkyloxy optionally substituted with cyano;
g) m is 0 and $R^3$ is cyano or aminocarbonyl;
h) m is 2 and $R^4$ is $C_{1-6}$alkyl, halo, $C_{1-6}$alkyloxy, $C_{1-6}$alkyl substituted with cyano; in particular said $R^4$ substituents are placed in position 2 and 6 compared to the $X_1$ linker.

Also an interesting embodiment of the present invention are those compounds of formula (I), (I'), (I''), (I'''), (I'''') or (I''''') wherein n is 0, $R^{2a}$ is cyano, m is 2 and $R^3$ is $C_{2-6}$alkenyl substituted with cyano.

Also an interesting embodiment of the present invention are those compounds of formula (I), (I'), (I''), (I'''), (I'''') or (I''''') wherein n is 2, $R^3$ is cyano, m is 0 and $R^{2a}$ is $C_{2-6}$alkenyl substituted with cyano.

In general, compounds of formula (I) can be prepared by reacting an intermediate of formula (II) wherein $W_1$ represents a suitable leaving group, such as for example halogen, e.g. chloro and the like, with an intermediate of formula (III) in the presence of a suitable acid, such as for example camphor sulfonic acid, and a suitable solvent, such as for example tetrahydrofuran or an alcohol, e.g. 2-propanol.

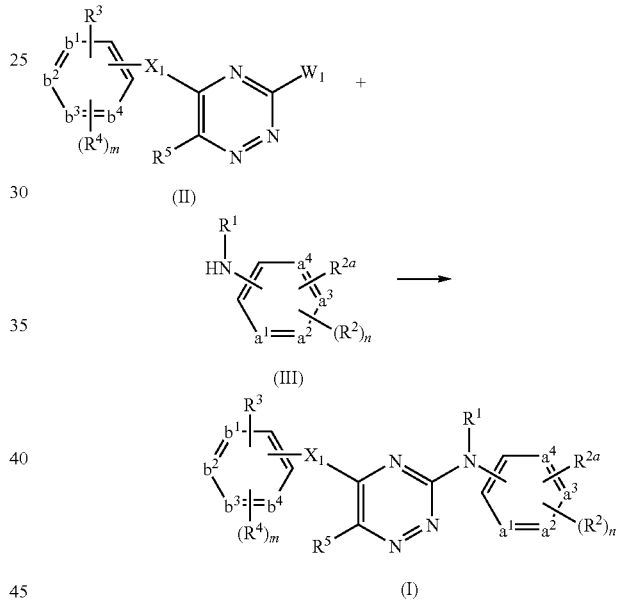

Compounds of formula (I) wherein $X_1$ represents $NR^1$, said compounds being represented by formula (I-a), can be prepared by reacting an intermediate of formula (IV) with an intermediate of formula (V) in the presence of POCl$_3$ and optionally in the presence of a suitable base, such as for example N,N-di-n-propylpropanamine.

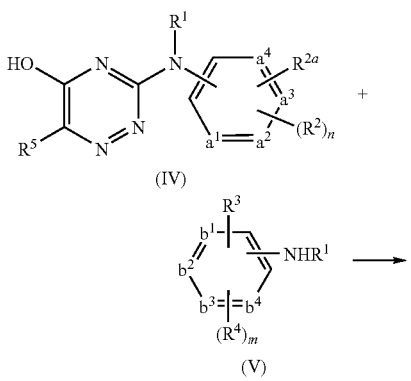

-continued

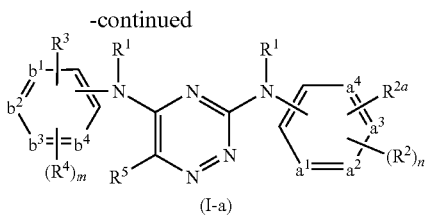

(I-a)

Compounds of formula (I) wherein $X_1$ represents O, said compounds being represented by formula (I-b), can be prepared by reacting an intermediate of formula (VI) wherein $W_2$ represents a suitable leaving group, such as for example halo, e.g. chloro and the like, with an intermediate of formula (VII) in the presence of a suitable base, such as for example $K_2CO_3$ or potassium t-butoxide (KO t-Bu), and a suitable solvent, such as for example acetone or tetrahydrofuran.

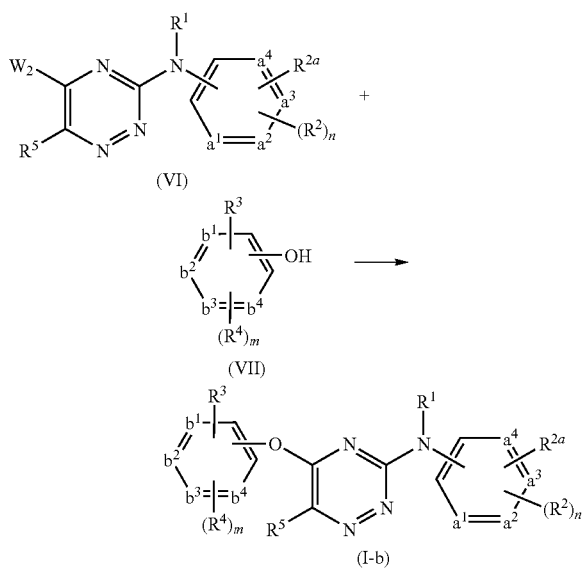

Compounds of formula (I-b) can also be prepared by reacting an intermediate of formula (IV) with an intermediate of formula (VII) in the presence of $POCl_3$, a suitable base, such as for example $K_2CO_3$ or potassium t-butoxide (KO t-Bu), and a suitable solvent, such as for example acetone or tetrahydrofuran.

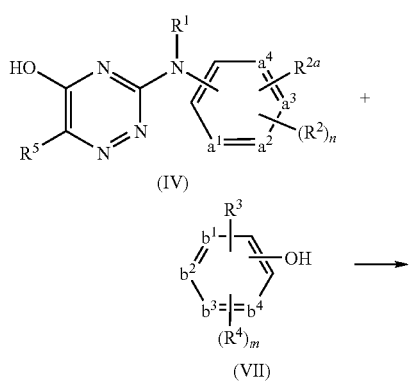

-continued

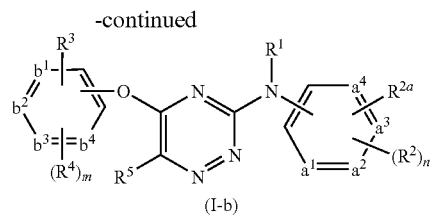

(I-b)

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkane metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^2$, $R^{2a}$, $R^3$ or $R^4$ is $C_{2-6}$alkenyl substituted with aminocarbonyl, can be converted into a compound of formula (I) wherein $R^2$, $R^{2a}$, $R^3$ or $R^4$ is $C_{2-6}$alkenyl substituted with cyano by reaction with $POCl_3$.

Compounds of formula (I) wherein m is zero, can be converted into a compound of formula (I) wherein m is other than zero and $R^4$ represents halo, by reaction with a suitable halo-introducing agent, such as for example N-chlorosuccinimide or N-borosuccinimide, or a combination thereof, in the presence of a suitable solvent, such as for example acetic acid.

Compounds of formula (I) wherein $R^3$ represents halo, may be converted into a compound of formula (I) wherein $R^3$ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or $R^7$ in the presence of a suitable base, such as for example N,N-diethyl-ethanamine, a suitable catalyst, such as for example palladium acetate in the presence of triphenylphosphine, and a suitable solvent, such as for example N,N-dimethylformamide.

Compounds of formula (I) wherein $R^{2a}$ represents halo, may be converted into a compound of formula (I) wherein $R^{2a}$ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or $R^7$ in the presence of a suitable base, such as for example N,N-diethyl-ethanamine, a suitable catalyst, such as for example palladium acetate in the presence of triphenylphosphine, and a suitable solvent, such as for example N,N-dimethylformamide.

Compounds of formula (I) wherein $R^1$ represents $C_{1-6}$alkyloxycarbonyl, can be converted into a compound of formula (I) wherein $R^1$ represents hydrogen, by reaction with a suitable acid, such as for example trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) can be prepared by reacting an intermediate of formula (VIII) wherein $W_1$ is defined as hereinabove, with an intermediate of formula (IX) in the presence of a suitable solvent, such as for example tetrahydrofuran, and optionally in the presence of a suitable base, such as for example $Na_2CO_3$.

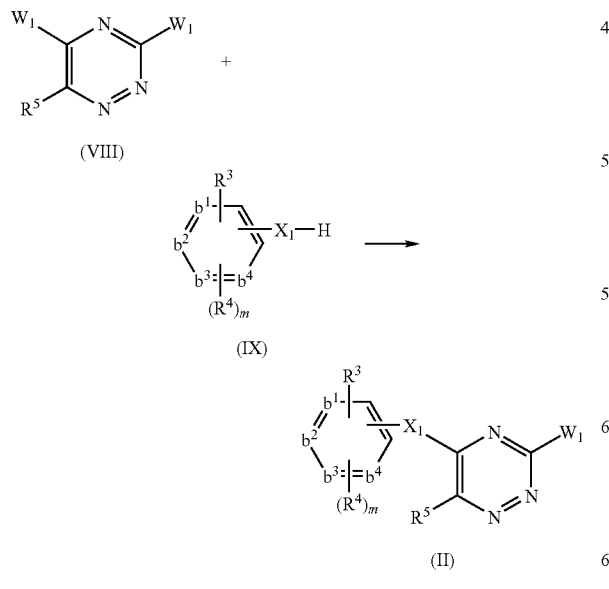

Intermediates of formula (VIII) wherein $W_1$ is chloro and $R^5$ is chloro, said intermediates being represented by formula (VIII-a), can be prepared by reacting an intermediate of formula (X) with $POCl_3$ and $PCl_5$ in the presence of a suitable base, such as for example N,N-diethylaniline.

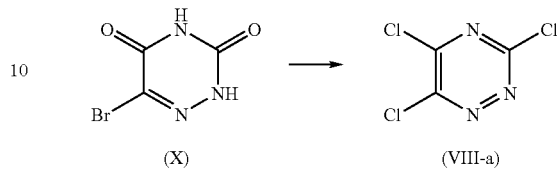

Intermediates of formula (X) can be prepared by reacting 1,2,4-triazine-3,5 (2H,4H) dione with $Br_2$ in the presence of a suitable solvent, such as for example $H_2O$.

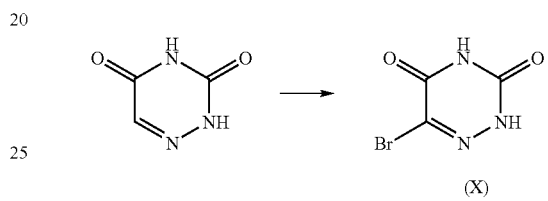

Intermediates of formula (III) or (V) wherein $R^1$ is hydrogen, said intermediates being represented by formula (III-a) and (V-a), can be prepared by reacting an intermediate of formula (XI) or (XII) with a suitable reducing agent, such as Fe, in the presence of $NH_4Cl$ and a suitable solvent, such as for example tetrahydrofuran, $H_2O$ and an alcohol, e.g. methanol and the like.

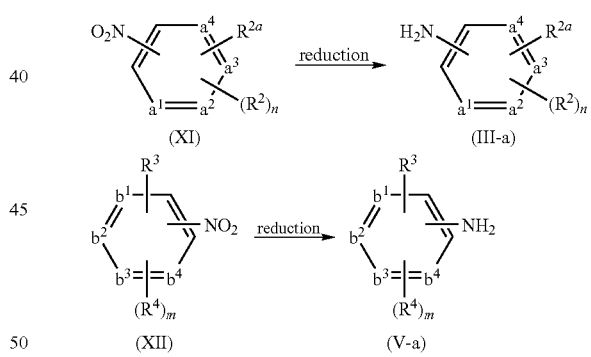

Intermediates of formula (III-a) or (V-a) wherein $R^{2a}$ respectively $R^3$ represents $C_{2-6}$alkyl substituted with cyano, said intermediates being represented by formula (III-a-1) and (V-a-1), can be prepared by reacting an intermediate of formula (XI-a) respectively (XII-a) with Pd/C in the presence of a suitable solvent, such as for example an alcohol, e.g. ethanol and the like.

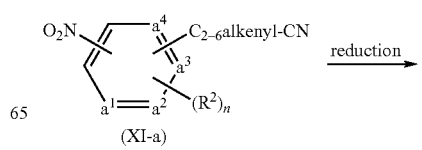

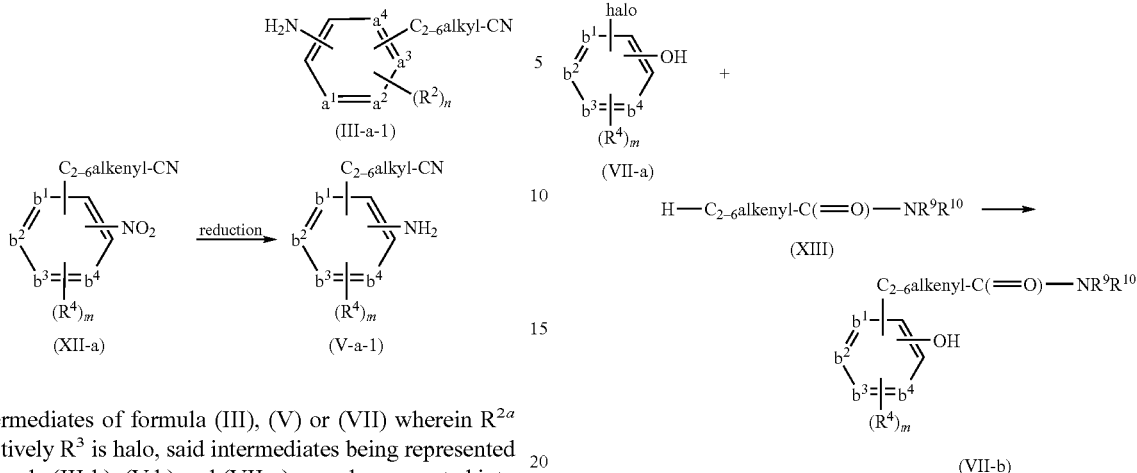

Intermediates of formula (III), (V) or (VII) wherein $R^{2a}$ respectively $R^3$ is halo, said intermediates being represented by formula (III-b), (V-b) and (VII-a), may be converted into an intermediate of formula (III) respectively (V) or (VII) wherein $R^{2a}$ respectively $R^3$ is $C_{2-6}$alkenyl substituted with $C(=O)NR^9R^{10}$, said intermediates being represented by formula (III-c), (V-c) and (VII-b) by reaction with an intermediate of formula (XIII) in the presence of $Pd(OAc)_2$, $P(o\text{-}Tol)_3$, a suitable base, such as for example N,N-diethylethanamine, and a suitable solvent, such as for example $CH_3$—CN.

Intermediates of formula (III-c), (V-c) and (VII-b) can also be prepared by reacting an intermediate of formula (III-f), (V-f) and (VII-c) with H—$NR^9R^{10}$ in the presence of oxalyl chloride and in the presence of a suitable solvent, such as for example N,N-dimethylformamide, $CH_2Cl_2$ and tetrahydrofuran.

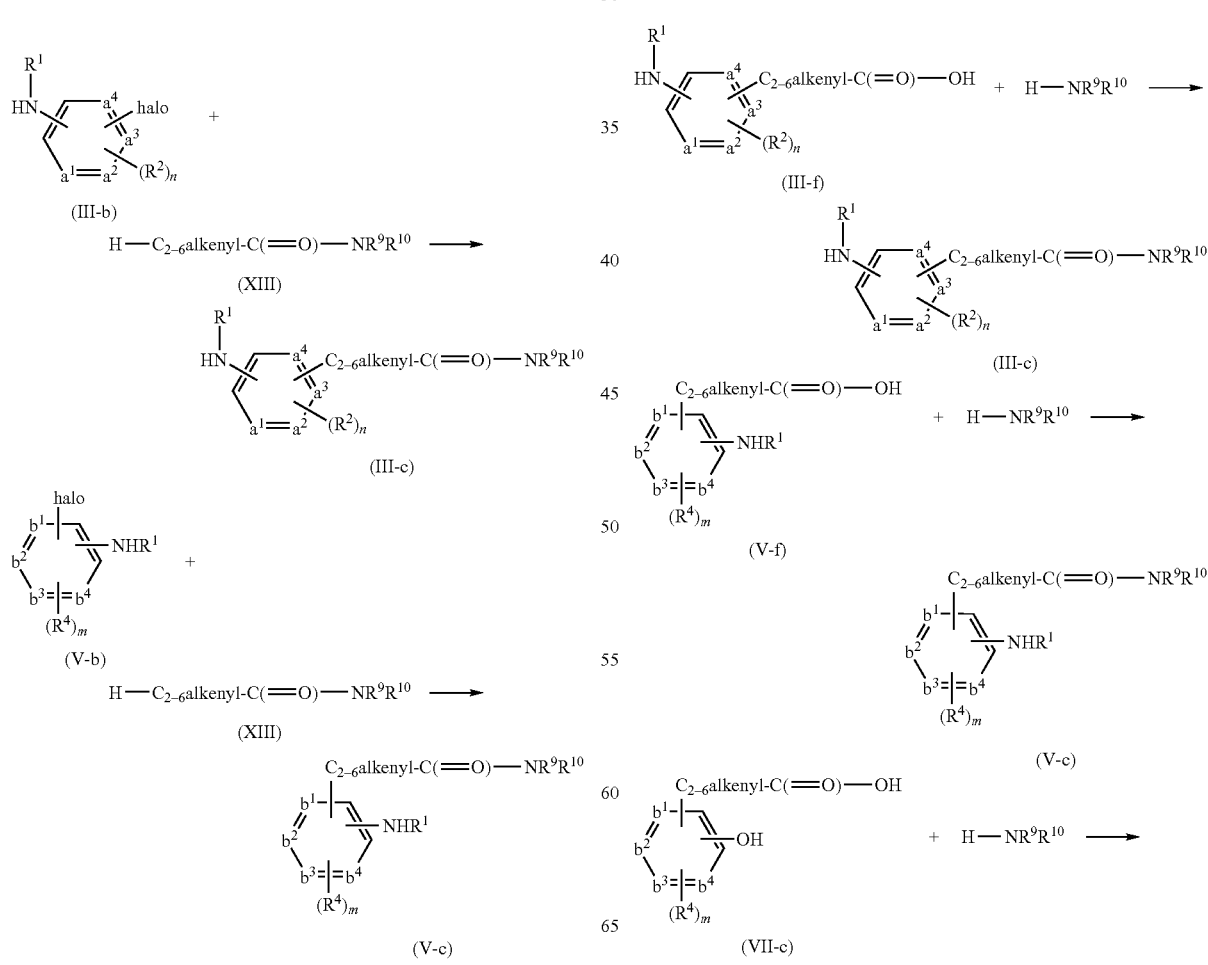

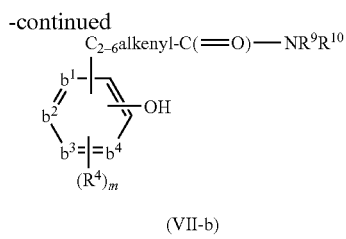

(VII-b)

Intermediates of formula (III-f), (V-f) and (VII-c) can be prepared by reacting an intermediate of formula (III-b), (V-b) and (VII-a), with H—C$_{2-6}$alkenyl-C(=O)—OH in the presence of Pd(OAc)$_2$, P(o-Tol)$_3$, a suitable base, such as for example N,N-diethylethanamine, and a suitable solvent, such as for example CH$_3$—CN.

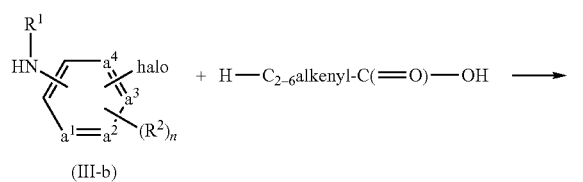

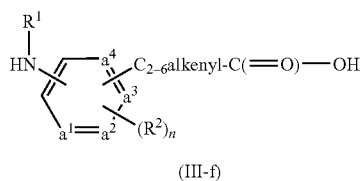

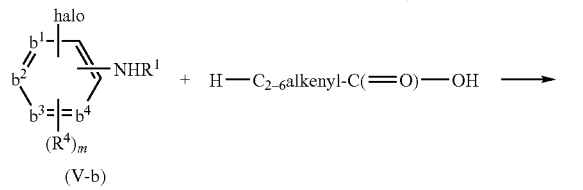

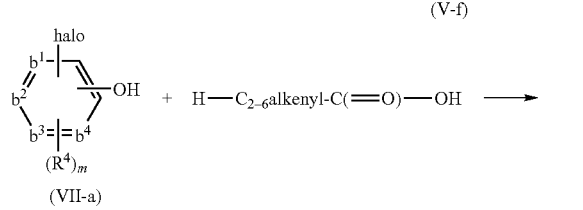

Intermediates of formula (III-b), (V-b) and (VII-a), may also be converted into an intermediate of formula (III) respectively (V) or (VII) wherein R$^{2a}$ respectively R$^3$ is C$_{2-6}$alkenyl substituted with CN, said intermediates being represented by formula (III-g), (V-g) and (VII-d) by reaction with H—C$_{2-6}$alkenyl-CN in the presence of Pd(OAc)$_2$, P(o-Tol)$_3$, a suitable base, such as for example N,N-diethylethanamine, and a suitable solvent, such as for example CH$_3$—CN.

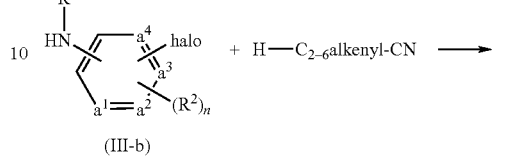

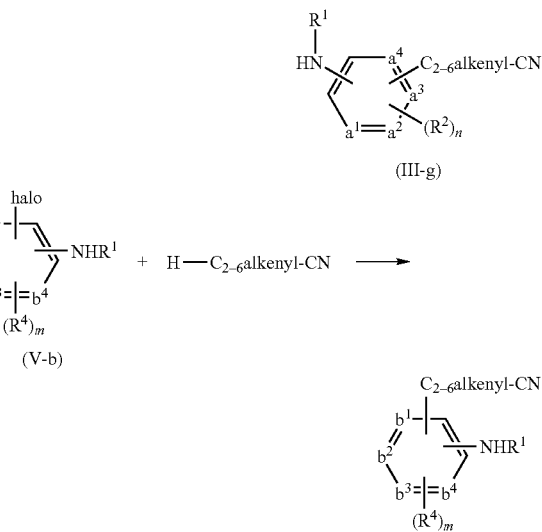

Intermediates of formula (III-b), (V-b) and (VII-a) can also be converted into an intermediate of formula (III-b)', (V-b)' and (VII-a)' by reaction with tributyl(1-ethoxyethenyl)stannane in the presence of Pd(OAc)$_2$, P(o-Tol)$_3$, a suitable base, such as for example N,N-diethylethanamine, and a suitable solvent, such as for example CH$_3$—CN.

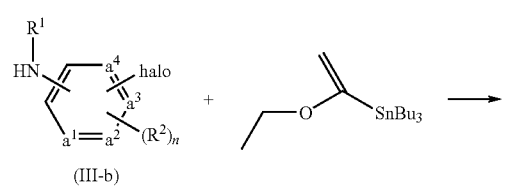

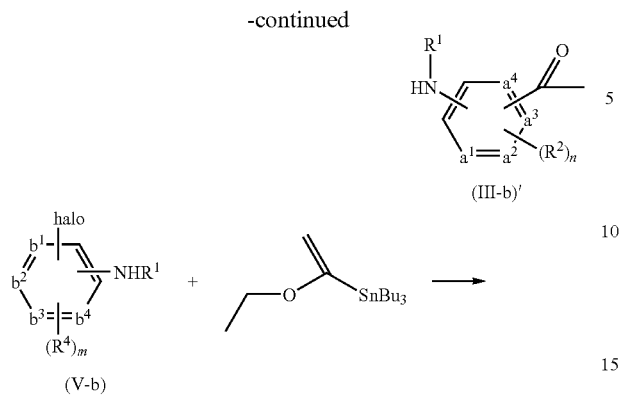

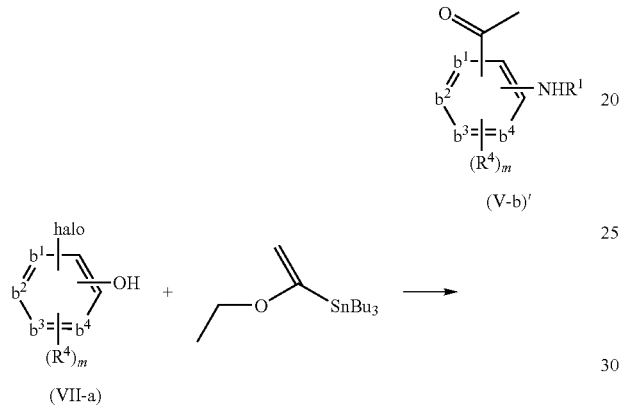

The intermediates of formula (III-b)', (V-b)' and (VII-a)' can be converted into an intermediate of formula (III-g-1), (V-g-1) and (VII-d-1) by reaction with diethylcyanomethylphosphonate in the presence of a suitable base, such as for example NaOCH$_3$, and a suitable solvent, such as for example tetrahydrofuran.

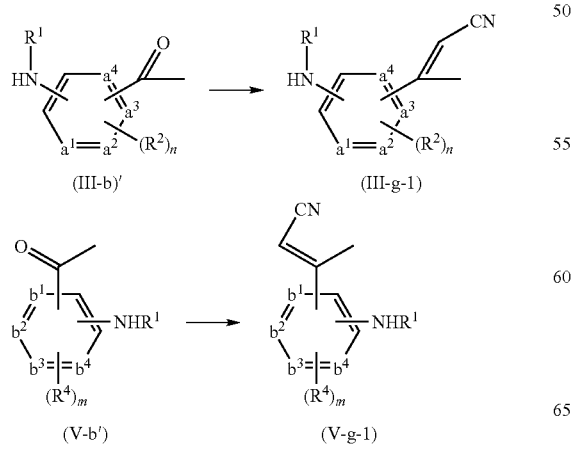

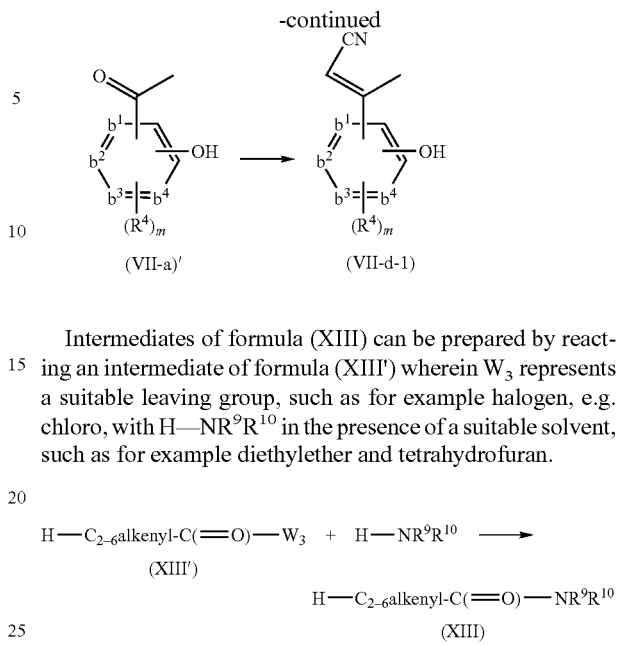

Intermediates of formula (XIII) can be prepared by reacting an intermediate of formula (XIII') wherein W$_3$ represents a suitable leaving group, such as for example halogen, e.g. chloro, with H—NR$^9$R$^{10}$ in the presence of a suitable solvent, such as for example diethylether and tetrahydrofuran.

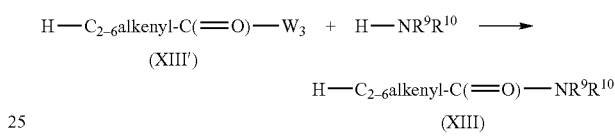

Intermediates of formula (III-b) and (V-b) may also be converted into an intermediate of formula (III-d) respectively (V-d) by reaction with an intermediate of formula (XIV) in the presence of Pd$_2$(dba)$_3$, P(t-Bu)$_3$, Na$_3$PO$_4$ and a suitable solvent, such as for example toluene. The intermediates of formula (III-d) respectively (V-d) may further be converted into an intermediate of formula (III-e) respectively (V-e) by reaction with NaCl in the presence of a suitable solvent, such as for example H$_2$O and dimethylsulfoxide.

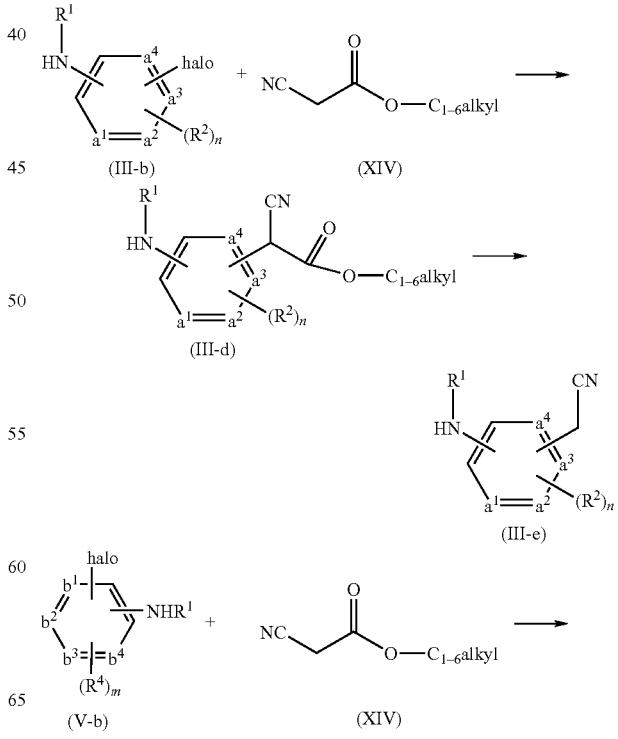

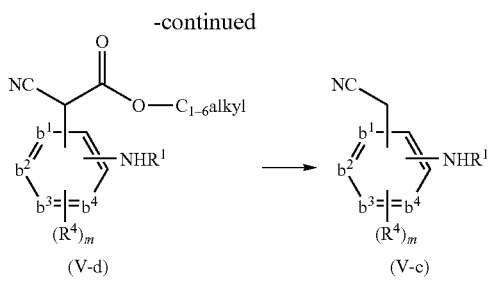

Intermediates of formula (XI) or (XII) wherein $R^{2a}$ respectively $R^3$ represents cyanovinyl, said intermediates being represented by formula (XI-b) and (XII-b), can be prepared by reacting an intermediate of formula (XV) respectively (XVI) with diethylcyanomethylphosphonate in the presence of a suitable base, such as for example $NaOCH_3$, and a suitable solvent, such as for example tetrahydrofuran.

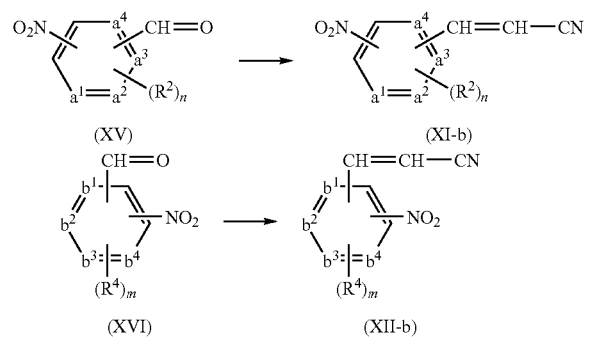

Intermediates of formula (XI) or (XII) wherein $R^{2a}$ respectively $R^3$ represents —C(CH$_3$)=CH—CN, said intermediates being represented by formula (XI-c) and (XII-c), can be prepared by reacting an intermediate of formula (XV') respectively (XVI') with diethylcyanomethylphosphonate in the presence of a suitable base, such as for example $NaOCH_3$, and a suitable solvent, such as for example tetrahydrofuran.

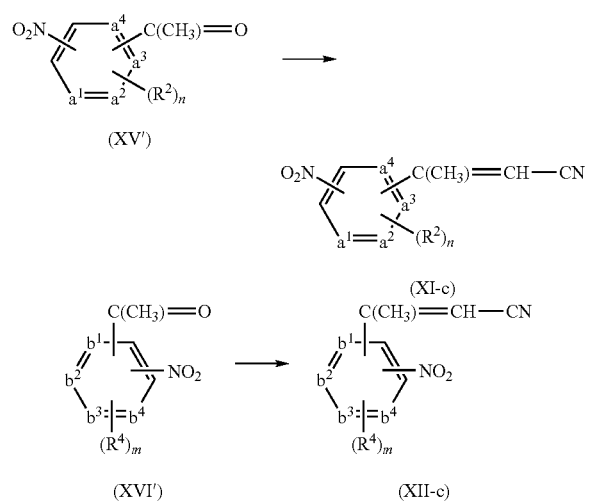

Intermediates of formula (XV) and (XVI) can be prepared by reacting an intermediate of formula (XVII) respectively (XVIII) with a suitable oxidizing agent, such as for example $MnO_2$, in the presence of a suitable solvent, such as for example acetone.

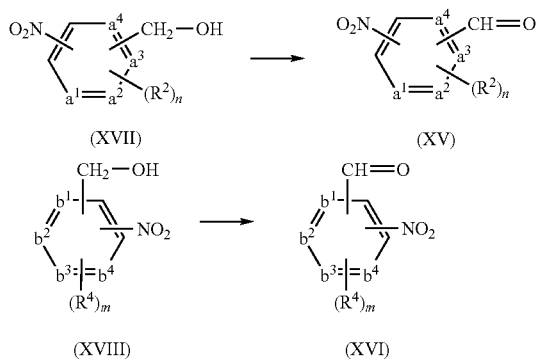

Intermediates of formula (XVII) and (XVIII) can be prepared by reacting an intermediate of formula (XIX) respectively (XX) with $NaBH_4$ in the presence of ethylchloroformate, a suitable base, such as for example N,N-diethylethanamine, and a suitable solvent, such as for example tetrahydrofuran.

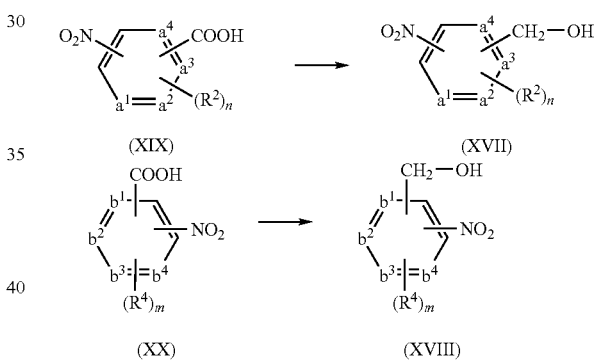

Intermediates of formula (XI) and (XII) wherein $R^{2a}$ respectively $R^3$ represent hydroxy, said intermediates being represented by formula (XI-d) respectively (XII-d), can be converted into an intermediate of formula (XI) respectively (XII) wherein $R^{2a}$ respectively $R^3$ represent $C_{1-6}$alkyloxy wherein the $C_{1-6}$alkyl may optionally be substituted with cyano, said $R^{2a}$ respectively $R^3$ being represented by P and said intermediates being represented by formula (XI-e) respectively (XII-e), by reaction with an intermediate of formula (XXI) wherein $W_4$ represents a suitable leaving group, such as for example halogen, e.g. chloro and the like, in the presence of NaI, a suitable base, such as for example $K_2CO_3$, and a suitable solvent, such as for example acetone.

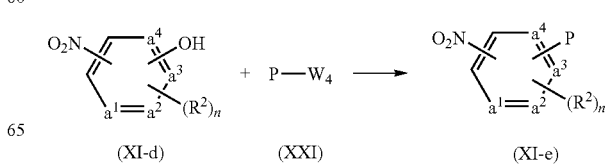

-continued

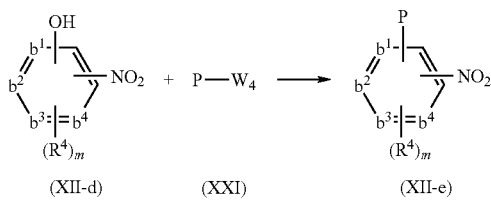

(XII-d)  (XXI)  (XII-e)

Intermediates of formula (XI) and (XII) can be prepared by reacting an intermediate of formula (XXII) respectively (XXIII) with NaNO₃ in the presence of CH₃SO₃H.

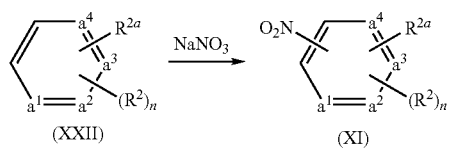

(XXII)  (XI)

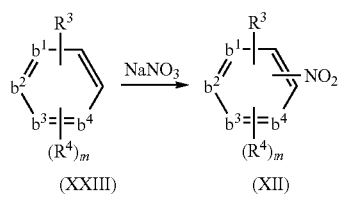

(XXIII)  (XII)

Intermediates of formula (IV) wherein $R^5$ is hydrogen respectively $C_{1-6}$alkyl, said intermediates being represented by formula (IV-a) respectively (IV-b), can be prepared by reacting an intermediate of formula (XXIV) with ethylglyoxalate respectively $C_{1-6}$alkylpyruvate in the presence of a suitable solvent, such as for example an alcohol, e.g. methanol.

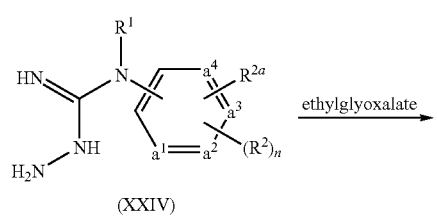

(XXIV)

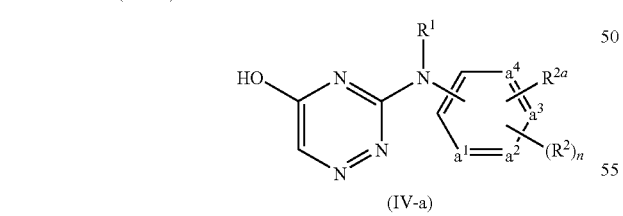

(IV-a)

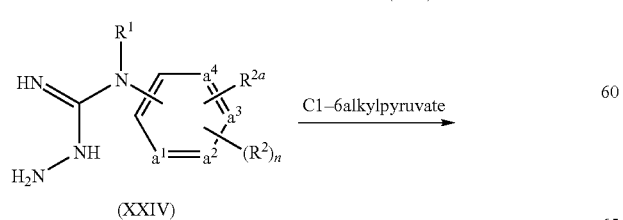

(XXIV)

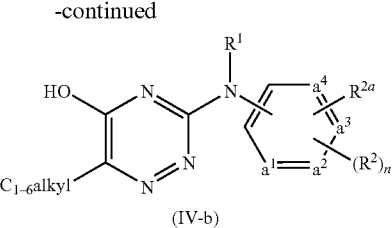

(IV-b)

Intermediates of formula (IV-a) can be converted into an intermediate of formula (IV) wherein $R^5$ represents bromo, said intermediate being represented by formula (IV-c), by reaction with Br₂ in the presence of a suitable base, such as for example N,N-diethylethanamine, and a suitable solvent, such as for example dimethylsulfoxide.

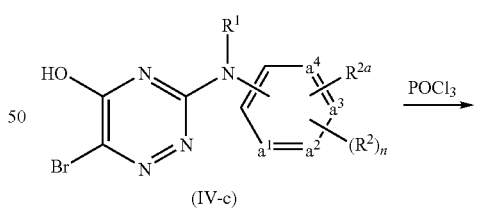

(IV-a)

(IV-c)

Intermediates of formula (IV-c) can be converted into an intermediate of formula (VI) wherein $R^5$ and $W_2$ represent chloro, said intermediate being represented by formula (VI-a), by reaction with POCl₃.

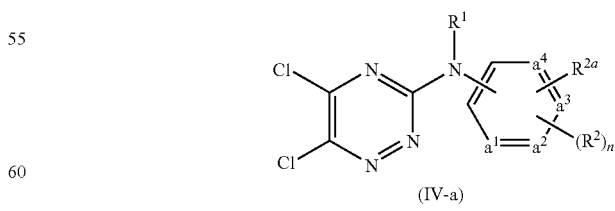

(IV-c)

(IV-a)

Intermediates of formula (XXIV) can be prepared by reacting an intermediate of formula (XXV) with hydrazine in the presence of a suitable solvent, such as for example N,N-dimethylformamide and an alcohol, e.g. methanol.

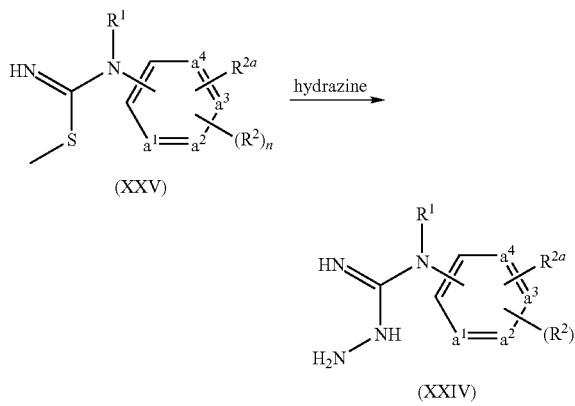

(XXV)

(XXIV)

Intermediates of formula (XXV) can be prepared by reacting an intermediate of formula (XXVI) with CH₃I in the presence of a suitable solvent, such as for example acetone.

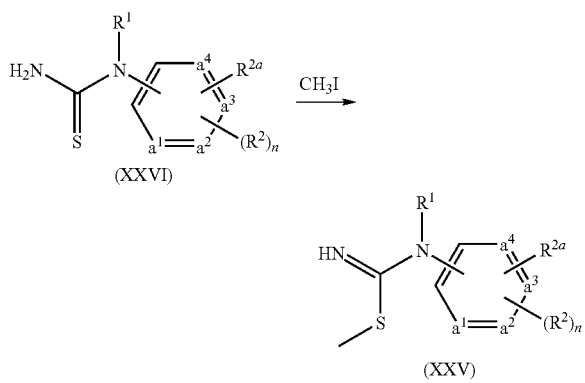

(XXVI)

(XXV)

Intermediates of formula (XXVI) wherein $R^1$ represents hydrogen, said intermediates being represented by formula (XXVI-a), can be prepared by reacting an intermediate of formula (XXVII) with ammonia in the presence of a suitable solvent, such as for example an alcohol, e.g. methanol.

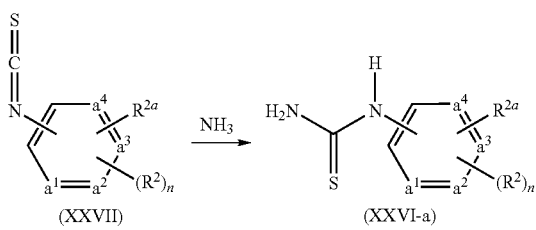

(XXVII)    (XXVI-a)

The compounds of formula (I), (I'), (I''), (I'''), (I'''') and (I''''') show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:

a) dissolving the compound of formula (I) and the water-soluble polymer in an appropriate solvent, optionally at elevated temperatures;

b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
   a) mixing a compound of formula (I) and an appropriate water-soluble polymer,
   b) optionally blending additives with the thus obtained mixture,
   c) heating and compounding the thus obtained blend until one obtains a homogenous melt,
   d) forcing the thus obtained melt through one or more nozzles; and
   e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodexttins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage.

Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-di-hydro -4-methyl-6H-dipyrido-[3,2-b:2',3'-e][1,4]diazepin-6-one), efavirenz, delavirdine, TMC-120, TMC-125 and the like; phosphonate reverse transcriptase inhibitors, e.g. tenofovir and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione; compounds of the α-APA (α-anilino phenyl acetamide) type e.g. α-[(2-nitrophenyl)amino]-2,6-di-chlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention.

EXPERIMENTAL PART

Hereinafter, "DMSO" is defined as dimethylsulfoxide, "TFA" is defined as trifluoroacetic acid, "DMF" is defined as N,N-dimethylformamide and "THF" is defined as tetrahydrofuran.

A. Preparation of the Intermediate Compounds

EXAMPLE A1 a) Preparation of Intermediate 1

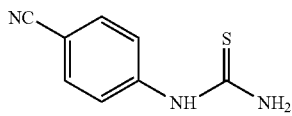

4-Isothiocyanatebenzonitrile (9.95 g) was suspended in methanol (100 ml) and NH$_3$, 26% aqueous (50 ml) was added. The reaction mixture was put in a cooler and filtered off, washed with methanol and Et$_2$O (2×) and dried at 35° C. under reduced pressure. Yield: 9.99 g (90.9%) of intermediate 1.

b) Preparation of Intermediate 2

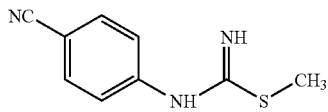

To intermediate 1 (9.99 g), CH$_3$I (3.87 ml) and acetone (150 ml) were added. The reaction mixture was stirred for 3 days. The reaction mixture was put in a cooler for 2 hours and then filtered off. The filtrate was washed with acetone and dried. Yield: 17.03 g (95.3%) of intermediate 2.

c) Preparation of Intermediate 3

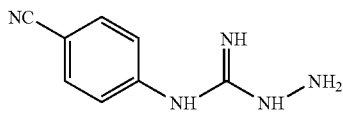

To intermediate 2 (17.03 g) was added hydrazine hydrate (3.11 ml) and methanol (150 ml). The reaction mixture was stirred for 3 days at 20° C. with a gas outlet. Yield: intermediate 3. The reaction mixture was used for the next reaction steps described in A2.a) and b).

EXAMPLE A2 a) Preparation of Intermediate 4

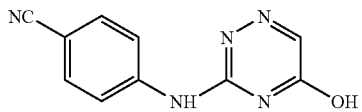

To two thirds (⅔) of the reaction mixture obtained in A1.c) was added ethyl glyoxalate 50% in toluene (14.11 ml) and the reaction mixture was stirred at 20° C. overnight The solvent was evaporated and the residue was dried under high vacuum. DMF (150 ml) was added and the mixture was heated at 80° C. overnight. DMF was evaporated and the residue was dried under high vacuum. The residue was stirred in methanol (150 ml) and put in a cooler overnight The precipitate was filtered off. Yield: 1.80 g (23.7%) of intermediate 4.

b) Preparation of Intermediate 5

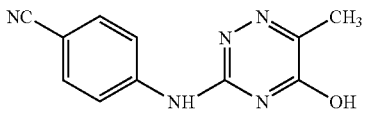

To one third (⅓) of the reaction mixture obtained in A1.c), was added methyl pyruvate (3.22 ml) and the reaction mixture was stirred at 20° C. overnight. The solvent was evaporated and the residue was dried under high vacuum. DMF (150 ml) was added and the mixture was heated at 80° C. overnight DMF was evaporated and the residue was dried under high vacuum. The residue was stirred in methanol (75 ml) and put in a cooler overnight. The precipitate was filtered off. Yield: 1.60 g (39.6%) of intermediate 5.

EXAMPLE A3 a) Preparation of Intermediate 6

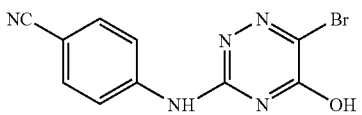

To a flask under Argon was added intermediate 4 (0.00469 mol), DMSO (25 ml), Br$_2$ (0.00704 mol), and Et$_3$N (0.00704 mol). The mixture was stirred at room temperature overnight. Water was added, and the mixture was stirred for 20 minutes. The reaction mixture was worked up to yield 0.30 g of intermediate 6. The solid was dried at 75° C. for 16 hours at 200 mm Hg.

b) Preparation of Intermediate 7

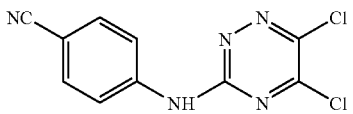

To a pressure vessel under Argon were added intermediate 6 (0.000616 mol) and POCl$_3$ (6 ml). The mixture was heated in an oil bath at 110° C. for 30 minutes, cooled, poured onto ice, stirred for 5 minutes, and filtered. Yield: 0.14 g of intermediate 7. The solid was dried at 200 mm Hg for 3 days at room temperature.

EXAMPLE A4 a) Preparation of Intermediate 8

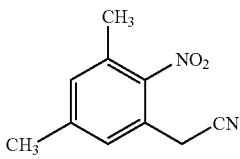

3,5-Dimethylbenzeneacetonitrile (3.0 g) was dissolved in MeSO$_3$H (10 ml) and cooled to 0° C. NaNO$_3$ (1.76 g) was added at once at 0° C. After 2 hours, the reaction mixture was poured into ice-H$_2$O under vigorous stirring. The product was extracted with EtOAc. The extract was washed with saturated aqueous NaHCO$_3$ (2×), dried with brine and Na$_2$SO$_4$ and purified using a mixture of EtOAc and n-heptane on silicagel. Yield: 2.00 g (51%) of intermediate 8.

b) Preparation of Intermediate 9

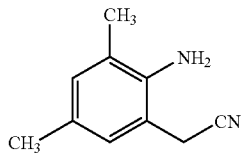

NH$_4$Cl (2.53 g) was dissolved in H$_2$O (20 ml) and Fe (1.59 g) was added. Intermediate 8 (1.80 g) dissolved in methanol (40 ml) and THF (20 ml) was added to the aqueous solution. The reaction mixture was stirred at 70° C. for 2 to 4 hours. The organic solvents were removed. The residue was stirred in EtOAc and the EtOAc was decanted; this procedure was repeated twice. The combined organic extracts were dried with brine and Na$_2$SO$_4$ and evaporated. Yield: 1.35 g of intermediate 9 (89%).

EXAMPLE A5 a) Preparation of Intermediate 10

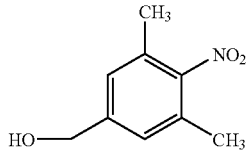

10.0 g of 3,5-dimethyl-4-nitrobenzoic acid and 7.10 ml (1 eq.) of Et$_3$N were dissolved in 40 ml of dry THF and cooled to −5° C. A solution of 5.14 ml of ethyl chloroformate in 10 ml of dry THF was added in the course of 10 minutes. The mixture was stirred for 0.5 hours at 20° C. The Et$_3$N—HCl was filtered off and the THF solution was added drop wise (30 minutes) to an aqueous solution (50 ml) of 4.07 g NaBH$_4$. This mixture was stirred for 4 hours at 20° C. and quenched with 1 N HCl until pH=2. The THF was evaporated and the residue was dissolved in EtOAc and washed with saturated aqueous NaHCO$_3$ and with brine and dried over Na$_2$SO$_4$. After evaporation, the residue was purified by silica column chromatography using heptane/EtOAc:3/1. Yield: intermediate 10 (68%).

b) Preparation of Intermediate 11

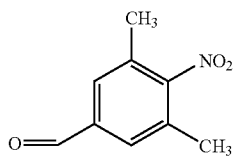

4.3 g of intermediate 10 was dissolved in 100 ml of acetone and 8.25 g (4 eq.) of MnO$_2$ were added. After 3 days stirring at 20° C., 2.06 g extra MnO$_2$ was added. Stirring was continued for 2 days. Then MnO$_2$ was filtered off, 100 ml heptane was added and the solution was again filtered and evaporated. The residue was dissolved in CH$_2$Cl$_2$ and filtered. The solvent was evaporated. Yield: 3.18 g (75%) of intermediate 11.

c) Preparation of Intermediate 12(E) and 13(Z)

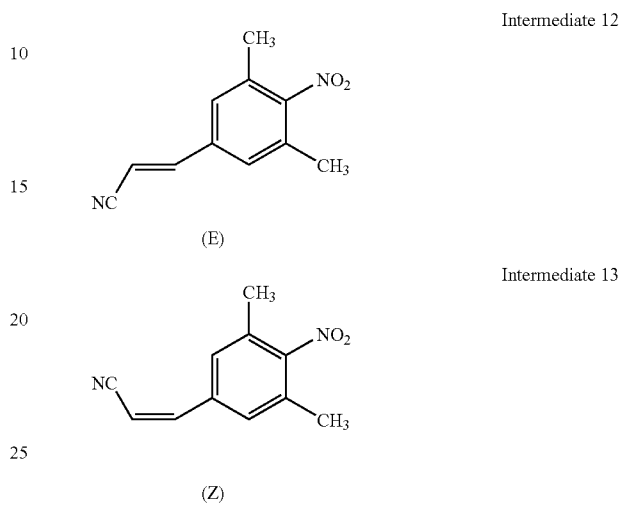

2.68 g of intermediate 11 and 2.65 g of diethyl cyanomethyl phosphonate were dissolved in 50 ml of dry THF and added to a suspension of 5.99 g of NaOMe in 30 ml of dry THF at 0° C. The reaction mixture was stirred for 1 hour at 0° C. The reaction mixture was quenched with 0.1 N HCl and the solvent was evaporated. EtOAc was added. The resulting solution was washed with saturated aqueous NaHCO$_3$ and dried with brine and Na$_2$SO$_4$ successively and evaporated. The residue was purified by silica column chromatography using heptane/EtOAc:5/1 as the eluent. Total yield of intermediate 12(E) and 13(Z) was 62%; the ratio of the intermediates 12 and 13=89/11.

EXAMPLE A6-1 a) Preparation of Intermediate 14

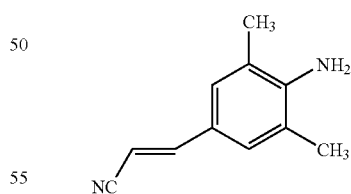

2.00 g of intermediate 12 was dissolved in 20 ml of THF and added to a solution of 2.65 g of NH$_4$Cl in 20 ml of H$_2$O. 40 ml of MeOH and 1.66 g of Fe were added. The reaction was stirred at 50° C. for 4 hours and after that cooled to ambient temperature. The solid material was filtered off and the filtrate was diluted with EtOAc and washed with saturated aqueous NaHCO$_3$ and dried with brine and with Na$_2$SO$_4$. The EtOAc was evaporated. Yield: 99% of intermediate 14.

b) Preparation of Intermediate 15

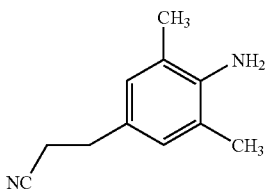

1) 1.68 g of intermediate 12 was hydrogenated using 0.88 g of 5% Pd/C in 200 ml of EtOH. After 4 hours, the Pd/C was filtered off and the filtrate was evaporated and stripped with $CH_2Cl_2$ to furnish intermediate 15 in 93% yield.

2) Intermediate 14 (3.44 g, 20 mmoles) was dissolved in EtOH (20 ml). 10% Pd/C (0.300 g) was added and the mixture was hydrogenated for 24 hours at room temperature after which period it was filtered on celite. The solvent was evaporated. Yield: 3.21 g of intermediate 15 (92%).

EXAMPLE A6-2 a) Preparation of Intermediate 30

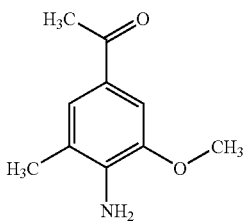

$Pd(OAc)_2$ (0.1 eq.), $P(o-Tol)_3$ (0.2 eq), $Et_3N$ (1.5 eq), 4-bromo-2-methoxy-6-methylbenzenamine (1.0 g; 4.63 mmol) and tributyl(1-ethoxyethenyl)stannane (1.0 eq.; 1.37 ml) were dissolved in dry MeCN (15 ml). $N_2$ was bubbled through the suspension for at least 20 minutes. Then a cooler was mounted strictly under nitrogen atmosphere. The reaction mixture was heated at 70° C. overnight. The reaction mixture was allowed to cool to 20° C. and was diluted with $CH_2Cl_2$ and washed with saturated aqueous $NaHCO_3$ (2×) and dried with brine and $Na_2SO_4$. The residue was sonicated in diisopropyl ether and filtered off. Yield: 0.22 g of intermediate 30 (26%).

b) Preparation of Intermediate 29

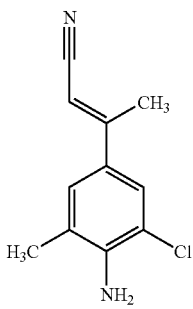

1-(4-amino-3-chloro-5-methylphenyl)ethanone (181 mg) (prepared according to A6-2a)) was added to NaOMe (133 mg) in dry THF (3 ml; 2.5 eq). Then diethyl cyanomethyl phosphonate (0.193 ml; 1.2 eq) were added. The mixture was stirred at room temperature. Extra phosphonate reagent (0.075 ml; 0.47 eq) was added and extra NaOMe (53 mg; 1.0 eq). The next day the same amounts extra reagent were added. The reaction mixture was diluted with EtOAc and washed with saturated aqueous $NaHCO_3$ and brine. The organic fraction was dried over $Na_2SO_4$ and evaporated. The residue was stirred and sonicated in diisopropyl ether/heptane 1/1 and filtered off. Yield: 0.11 g of intermediate 29 (54%).

EXAMPLE A7

Preparation of Intermediate 16

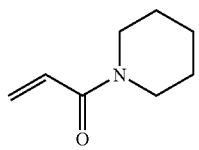

Acryloyl chloride (2.0 ml) was dissolved in dry $Et_2O$ (20 ml) and cooled to 0° C. Two equivalents of piperidine in $Et_2O$ (20 ml) was added dropwise. The reaction was stirred for 1 hour. The precipitate was filtered off and washed with ether. The organic fraction was washed with 0.5% $KHSO_4$ and with saturated aqueous $NaHCO_3$ and dried with brine and $Na_2SO_4$. The solvent was removed. Yield: 2.02 g (59%) of intermediate 16.

EXAMPLE A8 a) Preparation of Intermediate 17

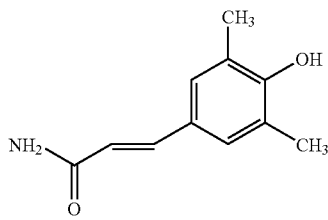

$Pd(OAc)_2$ (222 mg), $P(o-Tol)_3$ (604 mg), $Et_3N$ (2.07 ml), 4-bromo-2,6-dimethylphenol (2.0 g) and acrylamide (1.06 g) were dissolved in MeCN (15 ml) and $N_2$ was bubbled through the reaction mixture for at least 20 minutes. Then a cooler was mounted strictly under nitrogen atmosphere. The reaction mixture was heated at 70° C. overnight. The reaction mixture was allowed to cool to 20° C. and was diluted with $CH_2Cl_2$ and washed with saturated aqueous $NaHCO_3$ (2×) and dried with brine and $Na_2SO_4$. The residue was sonicated in diisopropyl ether and filtered off. Yield: 0.76 g of intermediate 17 (40%).

b) Preparation of Intermediate 18

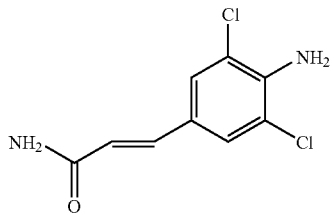

Pd(OAc)$_2$ (186 mg), P(o-Tol)$_3$ (505 mg), Et$_3$N (1.73 ml), 4-bromo-2,6-dichlorobenzeneamine (2.0 g) and acrylamide (885 mg) were dissolved in MeCN (15 ml) and N$_2$ was bubbled through the reaction mixture for at least 20 minutes. Then a cooler was mounted strictly under nitrogen atmosphere. The reaction mixture was heated at 70° C. overnight. The reaction mixture was allowed to cool to 20° C. and was diluted with CH$_2$Cl$_2$ and washed with saturated aqueous NaHCO$_3$ (2×) and dried with brine and Na$_2$SO$_4$. The residue was sonicated in diisopropyl ether and filtered off. Yield: 0.55 g of intermediate 18 (30%).

c-1) Preparation of Intermediate 31

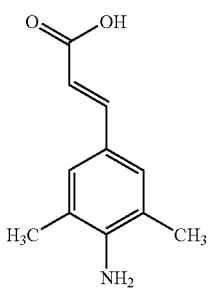

Pd(OAc)$_2$ (0.1 eq.), P(o-Tol)$_3$ (0.2 eq.), Et$_3$N (1.5 eq.), 4-bromo-2,6-dimethylbenzenamine (3.0 g; 14.99 mmol) and 2-propenoic acid (2.06 ml) were dissolved in dry MeCN (25 ml) and N$_2$ was bubbled through the reaction mixture for at least 20 minutes. Then a cooler was mounted strictly under nitrogen atmosphere. The reaction mixture was heated at 70° C. overnight. The reaction mixture was allowed to cool to 20° C. and was diluted with CH$_2$Cl$_2$ and washed with saturated aqueous NaHCO$_3$ (2×) and dried with brine and Na$_2$SO$_4$. The residue was sonicated in diisopropyl ether and filtered off. Yield: 0.76 g of intermediate 31 (40%) (E+Z).

c-2) Preparation of Intermediate 28

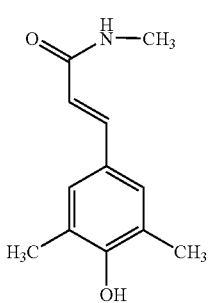

3-(4-hydroxy-3,5-dimethylphenyl)-2-propenoic acid (1.0 g) was suspended in CH$_2$Cl$_2$ (10 ml) and 1.2 equivalents oxalylchloride were added followed by three drops of DMF. The mixture was stirred overnight at room temperature, split into two equal batches and the solvent was evaporated. The oily residue was stripped with toluene. The residue was redissolved in dry THF (6 ml) and dropped onto methylamine in THF (2 M, 3.9 ml, 3 eq) and stirred overnight at ambient temperature. The reaction mixture was diluted with EtOAc and washed with saturated aqueous NaHCO$_3$ and the residue (brine, Na$_2$SO$_4$). The EtOAc was evaporated and the residue was sonicated in diisopropyl ether containing a few ml of EtOAc. The residue was filtered off and dried. Yield: 0.24 g of intermediate 28 (44%).

d) Preparation of Intermediate 32

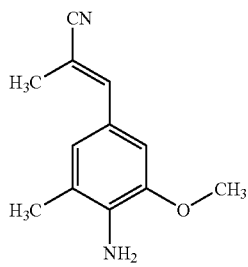

The reaction takes place in a closed vessel in a microwave oven. Pd(OAc)$_2$ (0.1 eq.), P(o-Tol)$_3$ (0.2 eq), Et$_3$N (1.5 eq), 4-bromo-2-methoxy-6-methylbenzenamine (2.16 g; 10 mmol) and 2-methyl-2-propenenitrile (1.5 eq.) were dissolved in MeCN (20 ml). N$_2$ was bubbled through the suspension for at least 20 minutes. The reaction mixture was heated at 150° C. for 10 minutes. The reaction mixture was allowed to cool to 20° C. and was diluted with EtOAc and washed with saturated aqueous NaHCO$_3$ (2×) and dried with brine and Na$_2$SO$_4$. The residue was used for flash chromatography (eluent: H/EA 4:1). Yield: 0.46 g of intermediate 32 (23%) (Z-isomer).

EXAMPLE A9

Preparation of Intermediate 20

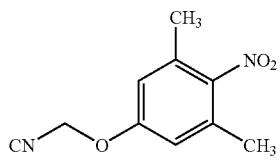

ClCH$_2$CN (0.80 ml), K$_2$CO$_3$ (2.31 g), NaI (126 mg) and 3,5-dimethyl-4-nitrophenol (prepared according to A4.a)(1.4 g) were dissolved in acetone (40 ml). The mixture was stirred overnight at 50° C. The residue was filtered off and the acetone was evaporated. The residue was dissolved in EtOAc and washed with saturated aqueous NaHCO$_3$ and dried with brine and Na$_2$SO$_4$. The EtOAc was evaporated. Yield: 1.91 g of intermediate 20 (99%)

EXAMPLE A10 a) Preparation of Intermediate 21

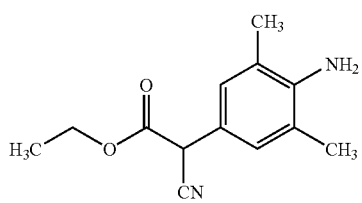

4-Bromo-2,6-dimethylbenzenamine (1.0 g), ethylcyanoacetate (0.59 ml), Pd$_2$(dba)$_3$ (0.058 mg), P(t-Bu)$_3$ (0.049 ml) and Na$_3$PO$_4$ (2.46 g) were dissolved in dry toluene (25 ml) and flushed 30 minutes with N$_2$. The reaction mixture was stirred overnight at 70° C. The reaction mixture was allowed to cool to 20° C. and filtered off. The toluene was purified on silica using 5% EtOAc in toluene. The product was sonicated in diisopropyl ether/n-heptane and filtered off. Yield: 0.45 g of intermediate 21 (65%).

b) Preparation of Intermediate 22

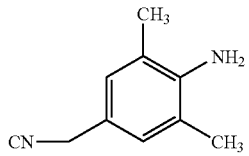

Intermediate 21 (450 mg) was dissolved in DMSO (16 ml) and H$_2$O (1 ml). NaCl (0.74 g) was added. The reaction mixture was heated for 3 hours at 140° C. The reaction mixture was then cooled to 20° C. and diluted with Et$_2$O. The organic solution was washed with brine (4×) and dried over Na$_2$SO$_4$. The combined brine extracts were extracted with Et$_2$O and this was combined with the first Et$_2$O fraction. The Et$_2$O was evaporated. Yield: 0.26 g of intermediate 22 (84%)

EXAMPLE A11 a) Preparation of Intermediate 23

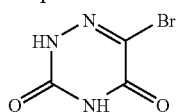

A mixture of 25 g of 6-azauracil, bromine (25 ml) and water (250 ml) was stirred at room temperature for 30 hours. The precipitate was filtered off. The filtrate was concentrated and the second precipitate was collected by filtration. The two precipitate fractions were combined and dried. Yield: 38.3 g of intermediate 23 (92%) (mp. 231-234° C.).

b) Preparation of Intermediate 24

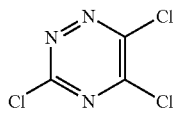

To 18 g of intermediate 23 in 150 ml of phosphorus oxychloride were added 39.2 g of phosphorus pentachloride and 38 ml of N,N-diethylaniline. The mixture was stirred at 120° C. for 5 hours after which period the excess of solvent was evaporated. The residue was several times extracted with carbon tetrachloride. After evaporation of the solvent, the remaining residue was put in the refrigerator where it solidified. Yield: 13 g of intermediate 24 (m.p. 57-60° C.).

EXAMPLE A12 a) Preparation of Intermediate 25

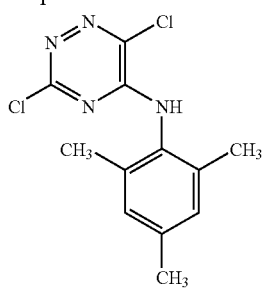

To a solution of intermediate 24 (0.560 g) in dry THF (30 ml) at −78° C. under nitrogen atmosphere was added 2,4,6-trimethylaniline (0.418 g). The reaction mixture was allowed to reach room temperature and was further stirred overnight at this temperature. The solvent was evaporated. The resulting residue was suspended in an aqueous solution of Na$_2$CO$_3$ and extracted with methylene chloride. The methylene chloride solution was dried over MgSO$_4$ and evaporated. The residue was chromatographed on a silica gel column using methylene chloride as eluent. Yield: 0.467 g of intermediate 25 (55%).

b) Preparation of Intermediate 26

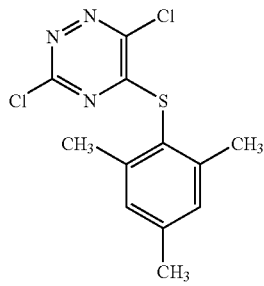

To a solution of intermediate 24 (0.560 g) in dry THF (30 ml) at −78° C. under nitrogen atmosphere was added 2,4,6-trimethylbenzenethiol (0.457 g) and sodium carbonate (0.318 g). The reaction mixture was allowed to reach room temperature and was further stirred overnight at this temperature. The solvent was evaporated. The resulting residue was suspended in water and extracted with methylene chloride. The methylene chloride solution was dried over MgSO$_4$ and evaporated. The residue was chromatographed on a silica gel column using methylene chloride as eluent. Yield: 0.612 g of intermediate 26 (68%).

EXAMPLE A13

Preparation of Intermediate 33

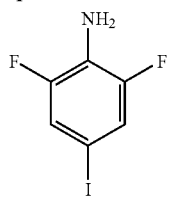

2,6-Difluorobenzenamine (3.0 g, 22.56 mmoles) was dissolved in acetic acid (10 ml). Iodine monochloride (3.581 g, 22.56 mmoles) was added to the solution. The mixture was stirred for 15 minutes at room temperature. After evaporation of the solvent, the residue was treated with an aqueous solution of sodium carbonate. The aqueous solution was extracted with dichloromethane. The organic extract was dried over MgSO$_4$ and was evaporated. Yield: 95% of intermediate 33.

EXAMPLE A14 a) Preparation of Intermediate 34

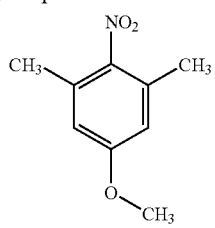

1-Methoxy-3,5-dimethylbenzene (4.12 g, 30 mmoles) was dissolved in acetic acid (20 ml). To this solution was added dropwise a mixture of nitric acid (1.26 ml, 30 mmoles) and concentrated sulfuric acid (1.9 ml, 35 mmoles). The mixture was heated at 70° C. for 15 minutes. After cooling, water was added and the mixture was extracted with dichloromethane.

The organic extract was dry and evaporated. The resulting residue was purified by column chromatography (30% heptane in CH$_2$Cl$_2$). Yield: 1.91 g of intermediate 34 (35%).

b) Preparation of Intermediate 35

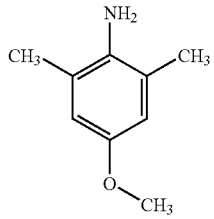

To a solution of intermediate 34 (1.81 g, 10 mmoles) in ethanol (20 ml) was added tin (II) chloride dihydrate (11.51 g, 50 mmoles) and the mixture was refluxed overnight. Upon cooling, ice was added to the reaction mixture followed by basification with 2N NaOH. The mixture was filtered and the filtrate was concentrated under reduced pressure. The aqueous solution was extracted with dichloromethane (4×30 ml). The organic layers were combined and dried over anhydrous MgSO$_4$ and the solvent was removed under reduced pressure. The residue was purified on a silica gel column chromatography (CH$_2$Cl$_2$ as eluent). Yield: 1.18 g of intermediate 35 (78%).

B. Preparation of the Final Compounds

EXAMPLE B1 a) Preparation of Compound 1

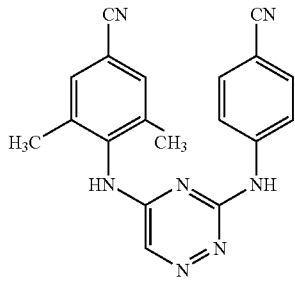

To intermediate 4 (prepared according to A2.a) (0.0019 mol) under Argon in POCl$_3$ (4 ml) was added N(n-Pr)$_3$ (0.39 ml). The reaction mixture was stirred at room temperature for one hour. 4-amino-3,5-dimethylbenzonitrile (0.0028 mol) was added and stirring at room temperature was continued for 16 hours. The reaction mixture was poured onto ice, then extracted with CH$_2$Cl$_2$ and evaporated. The residue was purified by flash column chromatography, eluting with 0,5% MeOH: CH$_2$Cl$_2$ to afford 0.27 g of residue. The residue was purified by reversed-phase HPLC (gradient of 0.1% TFA in water and 0.1% TFA in CH$_3$CN). Yield: 0.030 g of compound 1.

b) Preparation of Compound 36

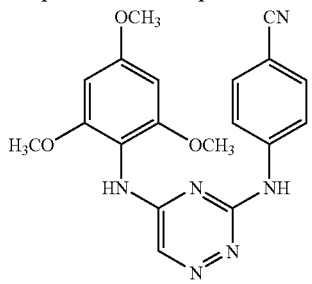

Intermediate 4 (100 mg) was added to 3 ml of POCl$_3$ at 0° C. 2,4,6-trimethoxybenzenamine (0.13 g) was added and the reaction mixture was stirred for 3 to 5 days. The ice bath was allowed to melt during the first couple of hours. After that, the POCl$_3$ suspension was dropped to 200 ml of vigorously stirred diisopropyl ether. The solid material was filtered off and washed with diisopropyl ether. The residue was immediately stirred in EtOAc/saturated aqueous NaHCO3 (1/1) (200 ml) for 1 hour. The EtOAc was dried using brine and Na$_2$SO$_4$ successively and evaporated. The residue was purified by preparative TLC using CH$_2$Cl$_2$/MeOH (95/5) as the eluent or by precipitation in CH$_2$Cl$_2$/MeOH. Yield. 0.01 g of compound 36 (8%).

c) Preparation of Compound 58

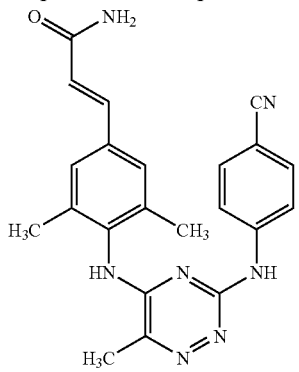

Intermediate 5 (prepared according to A2.b) (100 mg) was added to 3 ml of POCl$_3$ at 0° C. Intermediate 31

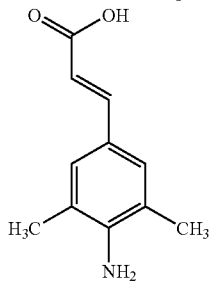

(prepared according to A8.c-1) (0.17 g) was added and the reaction mixture was stirred for 3 to 5 days. The ice bath was allowed to melt during the first couple of hours. The reaction mixture was poured onto heptane. The heptane was decanted. The residue was added at once to a large excess of 0.5 N NH$_3$ in dioxane containing 10 eq. DIPEA (diisopropylethylamine). The mixture was stirred overnight. The residue was filtered off and stirred in EtOAc/saturated aqueous NaHCO$_3$. The organic fraction was dried (brine, Na$_2$SO$_4$) and evaporated. The product was purified by preparative-TLC using CH$_2$Cl$_2$/MeOH 9/1 as the eluent. Yield: 0.01 g of compound 58 (3%).

EXAMPLE B2 a) Preparation of Compound 3

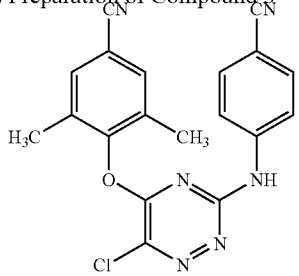

To a flask under Argon were added intermediate 7 (prepared according to A3.b) (0.000489 mol), K$_2$CO$_3$ (0.00244 mol), acetone (2 ml), and 4-hydroxy-3,5-dimethylbenzonitrile (0.000733 mol). The mixture was stirred at room temperature overnight The reaction mixture was evaporated, and water was added. The mixture was extracted with $CH_2Cl_2$, dried over $Na_2SO_4$, and evaporated. The aqueous phase was extracted again, dried, and evaporated. The two fractions were combined, and purified by flash column chromatography (0,2% methanol: $CH_2Cl_2$). The sample was recrystallized in $CH_3CN$, and filtered. Yield: 0.05 g of compound 3. The solid was dried at 0.2 mm Hg for 16 hours at room temperature.

b) Preparation of Compound 48

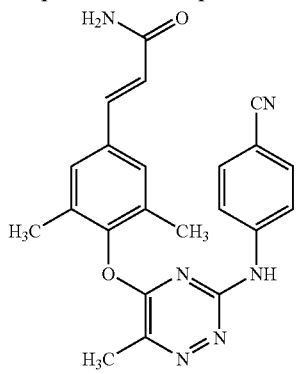

First step: Intermediate 5 (prepared according to A2.b) (100 mg) was added to 3 ml of $POCl_3$ at 0° C. The reaction mixture was stirred overnight. The ice bath was allowed to melt during the first couple of hours. After that, the $POCl_3$ suspension was dropped to 200 ml of vigorously stirred n-heptane. The solid material was filtered off and washed with heptane (2×). The residue was immediately stirred in EtOAc with crushed ice for 5 minutes. The EtOAc was dried using brine and $Na_2SO_4$ successively and evaporated. The residue was sonicated in n-heptane and filtered off. The triazine chloride prepared in this way was used in the next step.

Second step: KO-tBu (27 mg) was dissolved in ThF (6 ml) and added to a solution of intermediate 17 (1.5 eq.; ratio to the triazine chloride prepared above) (prepared according to A8a). After 1 hour, a solution of 60 mg of the triazine-chloride prepared above in THF was added to the deprotonated phenol and the mixture was stirred for 3 days. After that, the reaction mixture was poured onto EtOAc/$H_2O$/brine:2/1/1 (200 ml). The organic fraction was dried (brine and $Na_2SO_4$) and evaporated. The product was precipitated in acetone and filtered off. The residue was purified by preparative TLC using $CH_2Cl_2$/n-heptane/EtOAc/MeOH: 50/30/20/2 as the eluent. Yield: 0.05 g of compound48 (41%).

EXAMPLE B3 a) Preparation of Compound 44

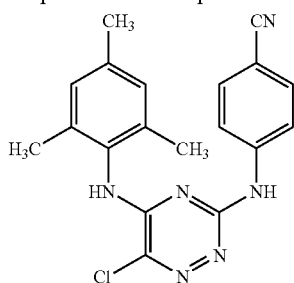

A mixture of intermediate 25 (prepared according to A12.a) (0.425 g), 4-aminobenzonitrile (0.272 g) and camphorsulfonic acid (CSA) (0.249 g) was refluxed for 48 hours in THF. After evaporation of the solvent, the residue was suspended in an aqueous solution of $Na_2CO_3$ and extracted with $CH_2Cl_2$. The dichloromethane solution was dried over $MgSO_4$ and evaporated. The resulting residue was purified by column chromatography using 10% ethyl acetate in dichloromethane as eluent. Yield: 0.454 g of compound 44.

b) Preparation of Compound 79

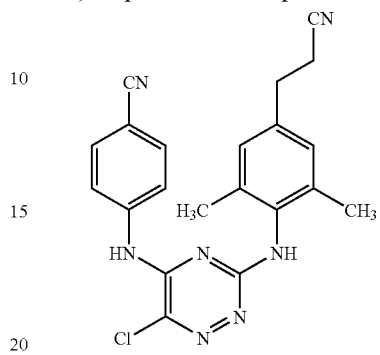

A mixture of

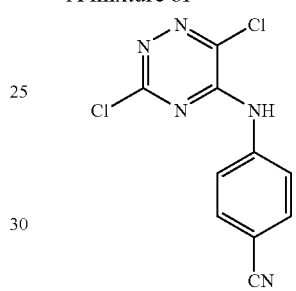

(prepared according to A12.b) (1 equiv.), intermediate 15 (prepared according to A6-1.b)) (1.5 equiv.), and camphor sulfonic acid (0.7 equiv.) was refluxed overnight in THF (oil bath 120° C.). After evaporation the residue was suspended in an aqueous solution of $Na_2CO_3$, and was extracted (3 times) with dichloromethane. After drying over $MgSO_4$ and evaporation of the dichloromethane extract, the residue was purified by column chromatography using 10% ethyl acetate in dichloromethane as eluent. Yield: 33% of final compound 79 (m.p. 266-267° C.).

EXAMPLE B4

Preparation of Compound 49

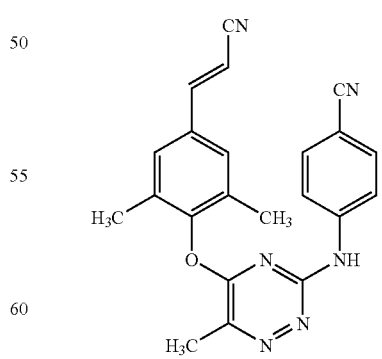

Compound 48 (prepared according B2.b) (40 mg) was dissolved in 2 ml of $POCl_3$ and stirred for 2 days. Then, the mixture was dropped into diisopropyl ether and filtered off and washed. Yield: 0.04 g of compound 49 (95%).

EXAMPLE B5 a) Preparation of Compound 74

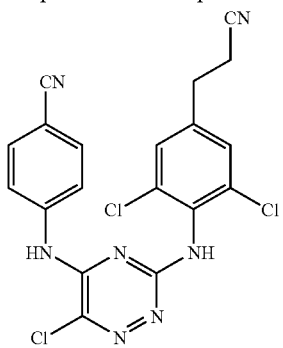

In a two necked flask protected with an aluminium foil and equipped with a condenser was dissolved compound 83 (prepared according to B3.b) (0.200 g; 0.53 mol) in acetic acid (5 ml). N-chlorosuccinimide (0.212 g, 1.60 mmol) was added. The mixture was degassed, and was heated at 120° C. After evaporation, the residue was dissolved in ethyl acetate. The solution was washed with an aqueous solution of $Na_2CO_3$ and water, dried over $MgSO_4$ and evaporated. The residue was chromatographed on a silica gel column (10% EtOAc in $CH_2Cl_2$). Yield: 24% of final compound 74 (m.p. 256-257° C.).

b) Preparation of Compound 75

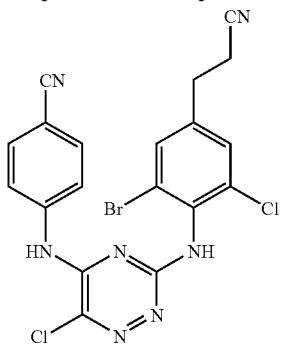

In a two necked flask protected with an aluminium foil and equipped with a condenser was dissolved compound 83 (prepared according to B3.b) (0.207 g, 0.55 mmole) in acetic acid. N-Bromosuccinimide (0.198 g, 1.1 mmole) was added. The mixture was degassed, and was heated at 110° C. for 15 minutes. After evaporation, the residue was dissolved in ethyl acetate. The solution was washed successively with an aqueous solution of $Na_2CO_3$, and water before drying over $MgSO_4$ and evaporation. The residue was dissolved in acetic acid in a two necked flask protected with an aluminium foil and equipped with a condenser as above. N-chlorosuccinimide (0.111 g, 0.83 mmole) was added. The mixture was degassed, and was heated at 110° C. for 15 minutes. After evaporation, the residue was dissolved in ethyl acetate. The solution was washed successively with an aqueous solution of $Na_2CO_3$ and water before drying over $MgSO_4$ and evaporation followed by purification of the residue by chromatography on a silica gel column (10% EtOAc in $CH_2Cl_2$). Yield: Final compound 75 (0.110 g, 41% yield) (m.p. 252-254° C.).

EXAMPLE B6

Preparation of Compound 62

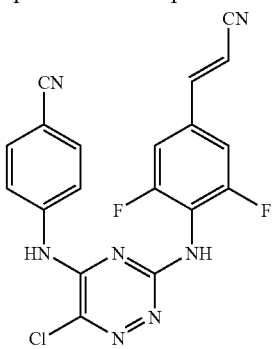

To a DMF solution of final compound 82 (prepared according to B3.b) (0.450 g, 0.928 mmoles) were added acrylonitrile (0.12 ml, 1.856 mmole), triethylamine (0.26 ml, 1.856 mmole), palladium acetate (0.0111 g, 0.023 mmole) and triphenylphosphine (0.0123 g, 0.046 mmole). After degassing the reaction mixture, it was flushed with nitrogen and the flask was stopped with a septum. It was then stirred overnight at 100° C.

After cooling, the reaction mixture was diluted with dichloromethane. The $CH_2Cl_2$ solution was washed with water (3 times) and was dried over $MgSO_4$ before evaporation. After evaporation, the residue was purified by column chromatography on a silica gel column (10% EtOAc in $CH_2Cl_2$. Yield: Final compound 62 (0.207 g, 54% yield) (m.p. 276-277° C.).

Table 1 lists the compounds that were prepared according to one of the above Examples (Ex.No.).

TABLE 1

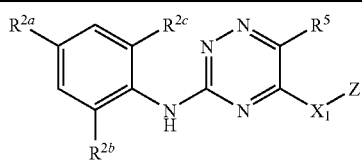

| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 1 | B1.a | CN | H | H | NH | H | 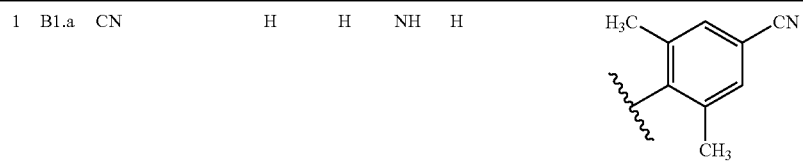 | |

TABLE 1-continued
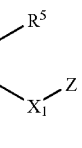
| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 7 | B1.b | CN | H | H | NH | H | 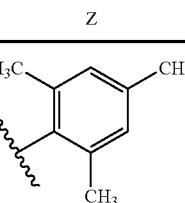 | |
| 8 | B1.b | CN | H | H | NH | H | 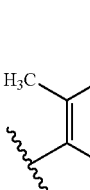 | |
| 9 | B1.b | CN | H | H | NH | H | 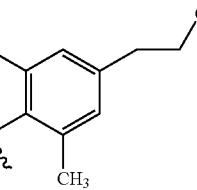 | |
| 10 | B1.b | CN | H | H | NH | H | 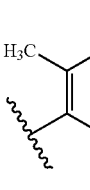 | |
| 14 | B1.b | CN | H | H | NH | H | 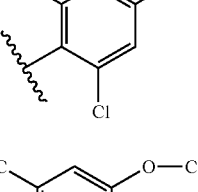 | |
| 15 | B1.b | CN | H | H | NH | H |  | |
| 24 | B1.b | CN | H | H | NH | H | 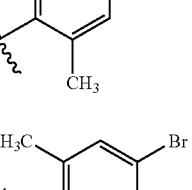 | |

TABLE 1-continued

| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 17 | B1.b | CN | H | H | NH | H | 4-tert-butyl-2,6-dimethylphenyl | |
| 36 | B1.b | CN | H | H | NH | H | 2,4,6-trimethoxyphenyl | |
| 37 | B1.b | CN | H | H | NH | H | 3,5-dimethyl-4-(N-methylcarbamoyl)phenyl | |
| 41 | B1.b | CN | H | H | NH | H | 4-(cyanomethoxy)-3,5-dimethylphenyl | |
| 43 | B1.b | CN | H | H | NH | H | 4-ethoxy-3,5-dimethylphenyl | |
| 52 | B1.b | CN | H | H | NH | H | 3,5-dimethyl-4-(N,N-dimethylcarbamoyl)phenyl | |

TABLE 1-continued

| Co. no. | Exp. no. | R²ᵃ | R²ᵇ | R²ᶜ | X₁ | R⁵ | Z | Phys. data |
|---|---|---|---|---|---|---|---|---|
| 51 | B1.b | CN | H | H | NH | H | 3,5-dimethyl-4-yl-N-ethylbenzamide | |
| 2 | B1.b | CN | H | H | NH | CH₃ | 3-(3,5-dimethyl-4-yl-phenyl)propanenitrile | |
| 5 | B1.b | CN | H | H | NH | CH₃ | 3,5-dimethyl-4-yl-benzonitrile | |
| 11 | B1.b | CN | H | H | NH | CH₃ | 4-methoxy-2,6-dimethylphenyl | |
| 12 | B1.b | CN | H | H | NH | CH₃ | 2,4,6-trimethylphenyl | |
| 13 | B1.b | CN | H | H | NH | CH₃ | (E)-3-(3,5-dimethyl-4-yl-phenyl)acrylonitrile | (E) |
| 16 | B1.b | CN | H | H | NH | CH₃ | 4-bromo-2,6-dimethylphenyl | |

TABLE 1-continued
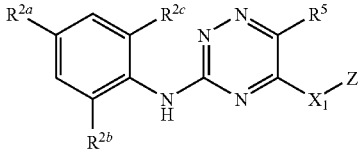
| Co. no. | Exp. no. | R²ᵃ | R²ᵇ | R²ᶜ | X₁ | R⁵ | Z | Phys. data |
|---|---|---|---|---|---|---|---|---|
| 18 | B1.b | CN | H | H | NH | CH₃ | 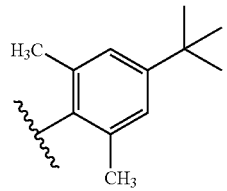 | |
| 19 | B1.b | CN | H | H | NH | CH₃ | 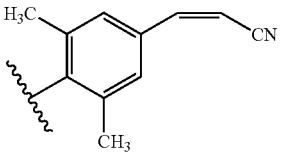 | (Z) |
| 20 | B1.b | CN | H | H | NH | CH₃ | 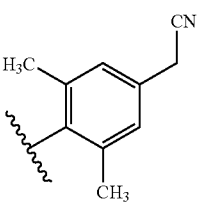 | |
| 21 | B1.b | CN | H | H | NH | CH₃ | 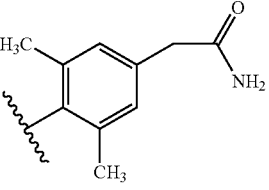 | |
| 22 | B1.b | CN | H | H | NH | CH₃ | 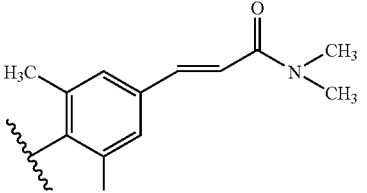 | |
| 23 | B1.b | CN | H | H | NH | CH₃ | 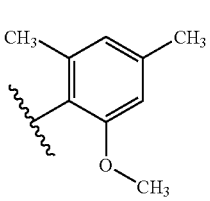 | |

TABLE 1-continued

| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 25 | B1.b | CN | H | H | NH | CH₃ | 2,4,6-trimethoxyphenyl | |
| 26 | B1.b | CN | H | H | NH | CH₃ | 3,5-dimethyl-4-[(E)-3-morpholino-3-oxoprop-1-enyl]phenyl | |
| 27 | B1.b | CN | H | H | NH | CH₃ | 2-(cyanomethyl)-3,5-dimethylphenyl | |
| 28 | B1.b | CN | H | H | NH | CH₃ | 3,5-dimethyl-4-[(E)-3-(methylamino)-3-oxoprop-1-enyl]phenyl | |
| 29 | B1.b | CN | H | H | NH | CH₃ | 3,5-dimethyl-4-[(E)-3-oxo-3-piperidinoprop-1-enyl]phenyl | |
| 30 | B1.b | CN | H | H | NH | CH₃ | 3,5-dimethyl-4-(N-methylcarbamoyl)phenyl | |

TABLE 1-continued

[Structure: R2a, R2b, R2c substituted phenyl-NH-triazine with R5 and X1-Z substituents]

| Co. no. | Exp. no. | R2a | R2b | R2c | X1 | R5 | Z | Phys. data |
|---|---|---|---|---|---|---|---|---|
| 31 | B1.b | CN | H | H | NH | CH3 | 4-(N,N-dimethylcarbamoyl)-3,5-dimethylphenyl | |
| 32 | B1.b | CN | H | H | NH | CH3 | 4-(N-ethylcarbamoyl)-3,5-dimethylphenyl | |
| 33 | B1.b | CN | H | H | NH | CH3 | 4-(2-cyanovinyl)-3,5-dimethoxyphenyl | |
| 34 | B1.b | CN | H | H | NH | CH3 | 4-(2-cyanovinyl)-3,5-dichlorophenyl | |
| 35 | B1.b | CN | H | H | NH | CH3 | 4-ethoxy-2,6-dimethylphenyl (via ring) – 3,5-dimethyl-4-(ethoxy)phenyl | |
| 38 | B1.b | CN | H | H | NH | CH3 | 3,5-dimethyl-4-(cyanomethoxy)phenyl | |

TABLE 1-continued

| Co. no. | Exp. no. | R²ᵃ | R²ᵇ | R²ᶜ | X₁ | R⁵ | Z | Phys. data |
|---|---|---|---|---|---|---|---|---|
| 39 | B1.b | CN | H | H | NH | CH₃ | 3,5-dimethyl-4-[(E)-3-oxo-3-(pyrrolidin-1-yl)prop-1-en-1-yl]phenyl | |
| 40 | B1.b | CN | H | H | NH | CH₃ | 4-(2-cyanoethyl)-2,6-dimethoxyphenyl | |
| 42 | B1.b | CN | H | H | NH | CH₃ | 4-[(E)-2-cyano-1-methylvinyl]-3,5-dimethylphenyl | |
| 55 | B1.b | CN | H | H | NH | CH₃ | 4-[(Z)-2-cyano-1-methylvinyl]-3,5-dimethylphenyl | (RS) |
| 58 | B1.c | CN | H | H | NH | CH₃ | 4-[(E)-3-amino-3-oxoprop-1-en-1-yl]-3,5-dimethylphenyl | |
| 59 | B1.b | CN | H | H | NH | CH₃ | 4-[(E)-3-(N-ethyl-N-methylamino)-3-oxoprop-1-en-1-yl]-3,5-dimethylphenyl | |

TABLE 1-continued

| Co. no. | Exp. no. | R$^{2a}$ | R$^{2b}$ | R$^{2c}$ | X$_1$ | R$^5$ | Z | Phys. data |
|---|---|---|---|---|---|---|---|---|
| 60 | B1.b | CN | H | H | NH | CH$_3$ | 3-methyl-5-methoxy-4-(2-cyanovinyl)phenyl | (E) |
| 61 | B1.b | CN | H | H | NH | CH$_3$ | 3,5-dichloro-4-(1-methyl-2-cyanovinyl)phenyl | (E) |
| 65 | B1.b | CN | H | H | NH | CH$_3$ | 3-methyl-5-chloro-4-(2-cyanovinyl)phenyl | (E) |
| 66 | B1.b | CN | H | H | NH | CH$_3$ | 3-methyl-5-methoxy-4-(1-methyl-2-cyanovinyl)phenyl | |
| 70 | B1.b | CN | H | H | NH | CH$_3$ | 3-chloro-5-methoxy-4-(2-cyanovinyl)phenyl | |
| 81 | B1.b | CN | H | H | NH | CH$_3$ | 3-methyl-5-methoxy-4-methyl-(2-cyano-2-methylvinyl)phenyl | |

TABLE 1-continued

| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 68 | B1.b | CN | H | H | NH | $CH_3$ | 3-Cl-4-(substituted)-5-OCH₃ phenyl with C(CH₃)=CH-CN | (E) |
| 67 | B1.b | CN | H | H | NH | $CH_3$ | 3,5-di-OCH₃-4-(substituted) phenyl with CH=CH-CN | (E) |
| 71 | B1.b | CN | H | H | NH | $CH_3$ | 3-CH₃-4-(substituted)-5-OCH₃ phenyl with C(CH₃)=CH-CN | |
| 69 | B1.b | CN | H | H | NH | $CH_3$ | 3-Cl-4-(substituted)-5-CH₃ phenyl with C(CH₃)=CH-CN | (E) |
| 6 | B1.b | H₂N-C(=O)- | H | H | NH | $CH_3$ | 3,5-di-CH₃-4-(substituted) phenyl with CN | |
| 54 | B3.a | CN | H | H | NH | Cl | 3,5-di-CH₃-4-(substituted) phenyl with CH=CH-CN | |

TABLE 1-continued
| Co. no. | Exp. no. | R$^{2a}$ | R$^{2b}$ | R$^{2c}$ | X$_1$ | R$^5$ | Z | Phys. data |
|---|---|---|---|---|---|---|---|---|
| 44 | B3.a | CN | H | H | NH | Cl | 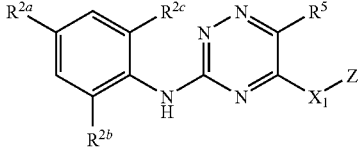 | |
| 4 | B2.b | CN | H | H | O | CH$_3$ | 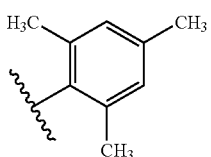 | |
| 47 | B2.b | CN | H | H | O | CH$_3$ | 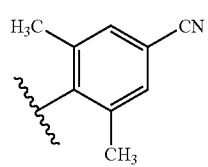 | |
| 48 | B2.b | CN | H | H | O | CH$_3$ | 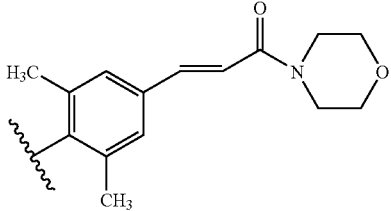 | |
| 49 | B4 | CN | H | H | O | CH$_3$ | 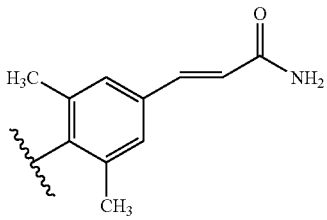 | |
| 50 | B2.b | CN | H | H | O | CH$_3$ | 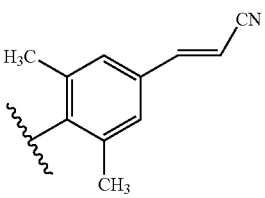 | |

TABLE 1-continued

| Co. no. | Exp. no. | R$^{2a}$ | R$^{2b}$ | R$^{2c}$ | X$_1$ | R$^5$ | Z | Phys. data |
|---|---|---|---|---|---|---|---|---|
| 56 | B2.b | CN | H | H | O | CH$_3$ | 3,5-dimethyl-4-yl phenyl -CH=CH-C(=O)NHCH$_3$ | |
| 57 | B2.b | CN | H | H | O | CH$_3$ | 3,5-dimethyl-4-yl phenyl -CH=CH-C(=O)N(CH$_3$)(C$_2$H$_5$) | |
| 3 | B2.a | CN | H | H | O | Cl | 3,5-dimethyl-4-cyanophenyl | |
| 46 | B3.a | CN | H | H | S | Cl | 2,4,6-trimethylphenyl | |
| 72 | B3.b | CN | CH$_3$ | CH$_3$ | NH | Cl | 4-cyanophenyl | |
| 45 | B3.b | CH$_3$ | CH$_3$ | CH$_3$ | NH | Cl | 4-cyanophenyl | |
| 64 | B3.b | —OCH$_3$ | CH$_3$ | CH$_3$ | NH | Cl | 4-cyanophenyl | |

TABLE 1-continued
[Structure: R²ᵃ, R²ᶜ, R⁵ substituted triazine with NH linker to phenyl bearing R²ᵇ, and X₁–Z group]
| Co. no. | Exp. no. | R²ᵃ | R²ᵇ | R²ᶜ | X₁ | R⁵ | Z | Phys. data |
|---|---|---|---|---|---|---|---|---|
| 83 | B3.b | —CH₂—CH₂—CN | H | H | NH | Cl | 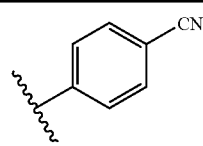 | |
| 79 | B3.b | —CH₂—CH₂—CN | CH₃ | CH₃ | NH | Cl | 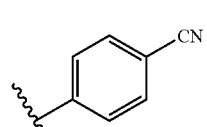 | (E + Z) |
| 74 | B5.a | —CH₂—CH₂—CN | Cl | Cl | NH | Cl | 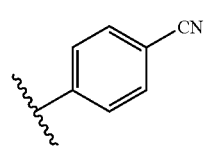 | |
| 73 | B5.a | —CH₂—CH₂—CN | Br | Br | NH | Cl | 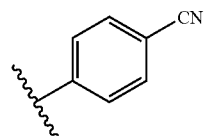 | |
| 75 | B5.b | —CH₂—CH₂—CN | Cl | Br | NH | Cl | 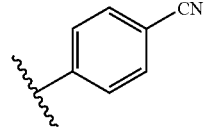 | |
| 62 | B6 | —CH=CH—CN | F | F | NH | Cl | 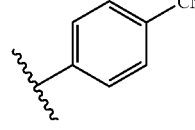 | (E) |
| 76 | B6 | —CH=CH—CN | Cl | Cl | NH | Cl | 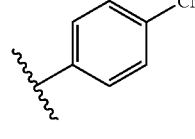 | (E) |
| 78 | B6 | —CH=CH—CN | Br | Br | NH | Cl | 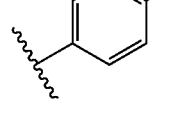 | (E + Z) |
| 77 | B6 | —CH=CH—CN | Cl | Br | NH | Cl | 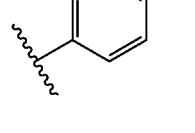 | (E) |

TABLE 1-continued

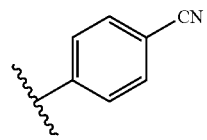

| Co. no. | Exp. no. | $R^{2a}$ | $R^{2b}$ | $R^{2c}$ | $X_1$ | $R^5$ | Z | Phys. data |
|---|---|---|---|---|---|---|---|---|
| 53 | B3.b | —CH=CH—CN | CH₃ | CH₃ | NH | Cl | 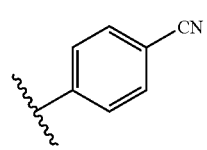 4-CN-phenyl | |
| 80 | B6 | —CH=CH—CN | OCH₃ | CH₃ | NH | Cl | 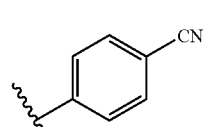 4-CN-phenyl | |
| 63 | B3.b | I | F | F | NH | H | 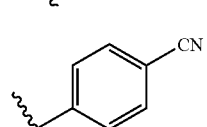 4-CN-phenyl | |
| 82 | B3.b | I | F | F | NH | Cl | 4-CN-phenyl | |

C. Analytical Part

1. Melting Points

TABLE 2

Melting points of compounds of the present invention.

| Compound no. | Result (° C.) |
|---|---|
| 3 | >300 |
| 44 | 272-273 |
| 46 | 295-296 |
| 53 | 274-276 |
| 54 | 281-282 |
| 62 | 276-277 |
| 63 | 305-306 |
| 72 | 260-261 |
| 73 | 256-257 |
| 74 | 254-257 |
| 75 | 252-254 |
| 80 | >338 |
| 79 | 266-267 |

2. [MH+] Results

[MH+] is the mass of the protonated compound (Chemical Ionisation Mass Spectrum)

TABLE 3

| Compound no. | [MH+] |
|---|---|
| 45 | 365 |
| 64 | 381 |
| 76 | 442 |
| 77 | 486 |
| 78 | 512 |

D. Pharmacological Example

The pharmacological activity of the present compounds was examined using one of the following tests (indicated in Table 4 in the most right column).

Test A

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}}$$ expressed in %, whereby $(OD_T)_{HIV}$ is the optical density measured with a given concentration of the test compound in HIV-infected cells; $(OD_C)_{HIV}$ is the optical density measured for the control unteated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in M). The ratio of $CC_{50}$ to $IC_{50}$ was defined as the selectivity index (SI).

Test B

An HIV-1 transformed T4-cell line, MT-4, which was previously shown (Koyanagi et al., *Int. J. Cancer,* 36, 445-451, 1985) to be highly susceptible to and permissive for HIV infection, served as the target cell line. In these cells, engineered with GFP (and an HIV-specific promotor), ongoing HIV-infection was measured fluorometrically. Cytotoxicity is measured in the same cells, but engineered with GFP under a constitutive promoter. The infection (or inhibition thereof) of HIV infected cells and the flourescence of mock-infected cells is assessed by the fluorescent GFP signal generated by the two above mentioned cell lines.

The 50% effective concentration ($EC_{50}$ in μM) was defined as the concentration of compound that reduced the fluorescence of HIV-infected cells by 50%. The 50% cytotoxic concentration ($CC_{50}$ in μM) was defined as the concentration of compound that reduced flourescence of the mock-infected cells by 50%.

Table 4 lists the $pIC_{50}$ ($-\log IC_{50}$), values for the compounds of formula (I). For example, a compound with a $IC_{50}$ value of $10^{-9}$M has a pIC50 value of 9.

TABLE 4

| Co. No. | $pIC_{50}$ (M) | $pCC_{50}$ | $pSI$ | Test |
|---|---|---|---|---|
| 1 | 8.7 | <4.0 | <-4.7 | A |
| 2 | 9.0 | <4.0 | <-5.0 | A |
| 3 | 8.3 | <4.0 | <-4.3 | A |
| 5 | 8.7 | <4.0 | <-4.7 | A |
| 7 | 9.3 | 5.5 | <-3.8 | A |
| 8 | 7.3 | <4.0 | <-3.3 | A |
| 9 | 7.8 | <4.0 | <-3.8 | A |
| 10 | 7.6 | <4.5 | <-3.1 | A |
| 11 | 9.2 | 5.5 | <-3.7 | A |
| 12 | 8.9 | 4.0 | <-4.9 | A |
| 13 | 8.2 | <4.0 | <-4.2 | A |
| 14 | 8.8 | <4.0 | <-4.8 | A |
| 15 | 8.8 | <4.0 | <-4.8 | A |
| 16 | 8.7 | 4.2 | -4.5 | A |
| 17 | 8.0 | <4.0 | <-4.0 | A |
| 18 | 8.1 | <4.0 | <-4.1 | A |
| 19 | 9.0 | 4.6 | -4.4 | A |
| 20 | 8.6 | <4.6 | <-4.0 | A |
| 22 | 7.1 | <4.6 | <-2.5 | A |
| 23 | 8.9 | 6.4 | -2.5 | A |
| 24 | 8.8 | <4.6 | <-4.2 | A |
| 25 | 8.6 | 4.4 | -4.3 | A |
| 27 | 8.3 | <4.0 | <-4.3 | A |
| 31 | 7.5 | <4.0 | <-3.5 | A |
| 33 | 8.6 | 5.4 | -3.2 | A |
| 34 | 8.6 | 5.0 | -3.6 | A |
| 35 | 8.2 | <4.6 | <-3.6 | A |
| 36 | 9.3 | <4.0 | <-5.3 | A |
| 37 | 7.0 | 4.3 | -2.7 | A |
| 38 | 8.9 | 4.7 | -4.2 | A |

TABLE 4-continued

| Co. No. | $pIC_{50}$ (M) | $pCC_{50}$ | $pSI$ | Test |
|---|---|---|---|---|
| 39 | 7.2 | <4.0 | <-3.2 | A |
| 40 | 8.6 | 5.0 | -3.6 | A |
| 41 | 7.6 | <4.6 | <-3.0 | A |
| 42 | 9.1 | 4.8 | -4.3 | A |
| 43 | 8.1 | <4.6 | <-3.5 | A |
| 44 | 8.6 | <4.6 | <-4.0 | A |
| 45 | 7.6 | <4.6 | <-3.0 | A |
| 46 | 7.9 | <4.6 | <-3.3 | A |
| 47 | 8.1 | <4.6 | <-3.5 | A |
| 48 | 9.2 | 4.6 | -4.6 | B |
| 50 | 8.9 | 4.7 | -4.2 | B |
| 51 | 7.2 | 5.1 | -2.1 | B |
| 52 | 8.6 | <4.6 | <-4.0 | B |
| 53 | 8.5 | 4.9 | -3.6 | B |
| 54 | 9.2 | 4.9 | -4.3 | B |
| 55 | 9.2 | 5.2 | -4.0 | B |
| 56 | 9.2 | 4.8 | -4.4 | B |
| 57 | 9.1 | 4.7 | -4.4 | B |
| 58 | 6.6 | 5.0 | -1.6 | B |
| 60 | 8.9 | 6.0 | -2.9 | B |
| 61 | 8.6 | 5.4 | -3.2 | B |
| 62 | 8.5 | 4.6 | -3.9 | B |
| 63 | 8.2 | 4.9 | -3.3 | B |
| 64 | 8.6 | 4.7 | -3.9 | B |
| 65 | 9.2 | 5.3 | -3.9 | B |
| 66 | 9.2 | 5.7 | -3.5 | B |
| 67 | 8.5 | 4.9 | -3.6 | B |
| 68 | 8.6 | 5.2 | -3.4 | B |
| 69 | 8.7 | 5.7 | -3.0 | B |
| 70 | 9.0 | 6.2 | -2.8 | B |
| 71 | 8.5 | 5.1 | -3.4 | B |
| 72 | 7.1 | <4.6 | <-2.5 | B |
| 73 | 8.5 | <4.6 | <-3.9 | B |
| 74 | 8.3 | <4.6 | <-3.7 | B |
| 75 | 8.5 | <4.6 | <-3.9 | B |
| 76 | 8.6 | <4.6 | <-4.0 | B |
| 77 | 8.5 | 5.0 | -3.5 | B |
| 78 | 8.6 | 5.1 | -3.5 | B |

The invention claimed is:

1. A compound of formula

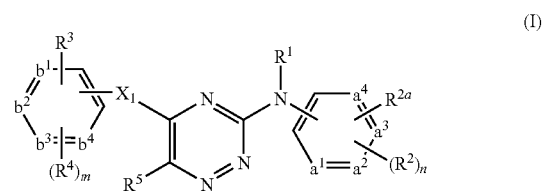

(I)

a N-oxide, a pharmaceutically acceptable acid or base addition salt or a stereochemically isomeric form thereof, wherein
-$a^1$=$a^2$-$a^3$=$a^4$- represents a bivalent radical of formula
—CH═CH—CH═CH— (a-1);
-$b^1$=$b^2$-$b^3$=$b^4$- represents a bivalent radical of formula
—CH═CH—CH═CH— (b-1);
n is 0, 1, 2, 3 or 4;
m is 0, 1, 2, 3 or 4;
$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
each $R^2$ independently is hydroxy; halo; $C_{1-6}$alkyl optionally substituted with one or more substituents each independently selected from halo, cyano or —C(═O)$R^6$; $C_{3-7}$cycloalkyl; $C_{2-6}$alkenyl optionally substituted with one or more substituents each independently selected from halo, cyano or —C(═O)$R^6$; $C_{2-6}$alkynyl optionally substituted with one or more substituents each independently selected from halo, cyano or —C(=O)R$^6$; C$_{1-6}$alkyloxycarbonyl; carboxyl; cyano; nitro; amino; mono- or di(C$_{1-6}$alkyl)amino; polyhalomethyl; polyhalomethylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$;

R$^{2a}$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_1$ is —NH—, —O—, or —S—;

X$_2$ is —NR$^1$—, —NH—NH—, —N=N—, —O—, —C(=O)—, —CHOH—, —S—, or —S(=O)$_p$—;

R$^3$ is cyano; aminocarbonyl; amino; C$_{1-6}$alkyl; halo; C$_{1-6}$alkyloxy wherein C$_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{1-6}$alkyl substituted with hydroxy and a second substituent selected from halo, cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R$^8$)—C$_{1-4}$alkyl; R$^7$ or —X$_3$—R$^7$;

X$_3$ is —NR$^1$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, —C$_{1-4}$alkanediyl-X$_{2b}$—C$_{1-4}$alkanediyl, —C(=N—OR$^8$)—C$_{1-4}$alkanediyl-; with X$_{2a}$ being —NH—NH—, —N=N—, —O—, —C(=O)—, —S—, —S(=O)$_p$—; and with X$_{2b}$ being —NH—NH—, —N=N—, —C(=O)—, —S—, —S(=O)$_p$—;

R$^4$ is halo; hydroxy; C$_{1-6}$alkyl optionally substituted with one or more substituents each independently selected from halo, cyano or —C(=O)R$^6$; C$_{2-6}$alkenyl optionally substituted with one or more substituents each independently selected from halo, cyano or —C(=O)R$^6$; C$_{2-6}$alkynyl optionally substituted with one or more substituents each independently selected from halo, cyano or —C(=O)R$^6$; C$_{3-7}$cycloalkyl; C$_{1-6}$alkyloxy; cyano; nitro; polyhaloC$_{1-6}$alkyl; polyhaloC$_{1-6}$alkyloxy; aminocarbonyl; mono- or di(C$_{1-4}$alkyl)aminocarbonyl; C$_{1-6}$alkyloxycarbonyl; C$_{1-6}$alkylcarbonyl; formyl; amino; mono- or di(C$_{1-4}$alkyl)amino or R$^7$;

R$^5$ is hydrogen; halo; aminocarbonyl; mono- or di(C$_{1-4}$alkyl)aminocarbonyl; amino; C$_{1-6}$alkyloxycarbonyl; C$_{1-6}$alkyloxycarbonylamino; polyhaloC$_{1-6}$alkyl; C$_{1-6}$alkyl optionally substituted with cyano, hydroxy, halo, C$_{1-6}$alkyloxy, C$_{1-6}$alkylthio or S(=O)$_p$—C$_{1-6}$alkyl; C$_{2-6}$alkenyl optionally substituted with cyano, hydroxy, halo, C$_{1-6}$alkyloxy, C$_{1-6}$alkylthio or S(=O)$_p$—C$_{1-6}$alkyl; C$_{2-6}$alkynyl optionally substituted with cyano, hydroxy, halo, C$_{1-6}$alkyloxy, C$_{1-6}$alkylthio or S(=O)$_p$—C$_{1-6}$alkyl;

R$^6$ is C$_{1-4}$alkyl, amino, mono- or di(C$_{1-4}$alkyl)amino or polyhaloC$_{1-4}$alkyl;

R$^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkyl;

R$^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$);

R$^8$ is hydrogen, C$_{1-4}$alkyl, aryl or arylC$_{1-4}$alkyl;

R$^9$ and R$^{10}$ each independently are hydrogen; hydroxy; C$_{1-6}$alkyl; C$_{1-6}$alkyloxy; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, R$^7$; with the proviso that R$^9$ and R$^{10}$ are not simultaneously hydroxy or C$_{1-6}$alkyloxy; or R$^9$ and R$^{10}$ may be taken together to form a bivalent radical of formula —CH$_2$—CH$_2$—CH$_2$—CH$_2$— (d-1)
—CH$_2$—CH$_2$—CH$_2$—CH$_2$—CH$_2$— (d-2)
—CH$_2$—CH$_2$—O—CH$_2$—CH$_2$— (d-3)
—CH$_2$—CH$_2$—S—CH$_2$—CH$_2$— (d-4)
—CH$_2$—CH$_2$—NR$^{12}$—CH$_2$—CH$_2$— (d-5)
—CH$_2$—CH=CH—CH$_2$— (d-6)

R$^{11}$ is cyano; C$_{1-4}$alkyl optionally substituted with C$_{1-4}$alkyloxy, cyano, amino, mono- or di(C$_{1-4}$alkyl) amino or aminocarbonyl; C$_{1-4}$alkylcarbonyl; C$_{1-4}$alkyloxycarbonyl; aminocarbonyl; mono- or di(C$_{1-4}$alkyl) aminocarbonyl;

83

$R^{12}$ is hydrogen or $C_{1-4}$alkyl;
$R^{13}$ and $R^{14}$ each independently are $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;
$R^{15}$ is $C_{1-6}$alkyl substituted with cyano or aminocarbonyl;
$R^{16}$ is $C_{1-6}$alkyl optionally substituted with cyano or aminocarbonyl, or $R^7$;
p is 1 or 2;
aryl is phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$ provided the following compounds
1,2,4-triazine-6-carboxylic acid, 3,5-bis[(4-methylphenyl)amino]-, ethyl ester;
N,N'-bis(4-chlorophenyl)-6-fluoro-1,2,4-triazine-3,5-diamine;
are not included.

2. A compound according to claim 1 wherein at least one of m or n is other than 0.

3. A compound according to claim 1 wherein the compound has the formula

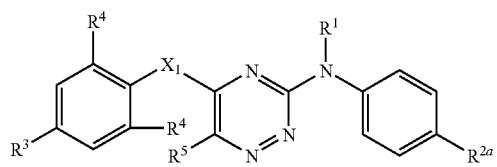

(I'''')

wherein $R^1$, $R^{2a}$, $R^3$, $R^4$, $R^5$ and $X_1$ are as defined in claim 1.

4. A compound as claimed in claim 1 wherein the compound has the formula

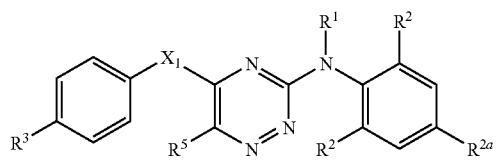

(I''''')

wherein $R^1$, $R^{2a}$, $R^3$, $R^4$, $R^5$ and $X_1$ are as defined in claim 1.

5. A compound according to claim 1 wherein $R^{2a}$ is cyano, aminocarbonyl, $C_{1-6}$alkyl, $C_{1-6}$alkyl substituted with cyano or aminocarbonyl, $C_{2-6}$alkenyl optionally substituted with cyano or aminocarbonyl.

6. A compound according to claim 1 wherein $R^5$ is hydrogen, $C_{1-6}$alkyl or halo.

7. A compound according to claim 1 wherein $R^{2a}$ or $R^2$ is halo, cyano, aminocarbonyl, $C_{1-6}$alkyloxy, $C_{1-6}$alkyl, $C_{1-6}$alkyl substituted with cyano or $C_{2-6}$alkenyl substituted with cyano.

8. A compound according to claim 1 wherein n is 0 or 2.

9. A compound according to claim 1 wherein $R^3$ is $C_{1-6}$alkyl; cyano; aminocarbonyl; mono or di($C_{1-4}$alkyl)aminocarbonyl; $C_{1-6}$alkyl substituted with cyano or aminocarbonyl; $C_{2-6}$alkenyl substituted with cyano or aminocarbonyl or mono- or di($C_{1-4}$alkyl)aminocarbonyl or C(=O)$NR^9R^{10}$

84 wherein $R^9$ and $R^{10}$ are taken together to form a bivalent radical of formula (d-1) to (d-6); halo; or $C_{1-6}$alkyloxy optionally substituted with cyano.

10. A compound according to claim 1 wherein m is 0 and $R^3$ is cyano or aminocarbonyl.

11. A compound according to claim 1 wherein m is 2 and $R^4$ is $C_{1-6}$alkyl, halo, $C_{1-6}$alkyloxy, $C_{1-6}$alkyl substituted with cyano.

12. A compound according to claim 1 wherein $R^{2a}$ is cyano, m is 2 and $R^3$ is $C_{2-6}$alkenyl substituted with cyano.

13. A compound according to claim 1 wherein n is 2, $R^3$ is cyano, m is 0 and $R^{2a}$ is $C_{2-6}$alkenyl substituted with cyano.

14. A compound according to claim 1 wherein $R^1$ is hydrogen.

15. A compound having the following structure:

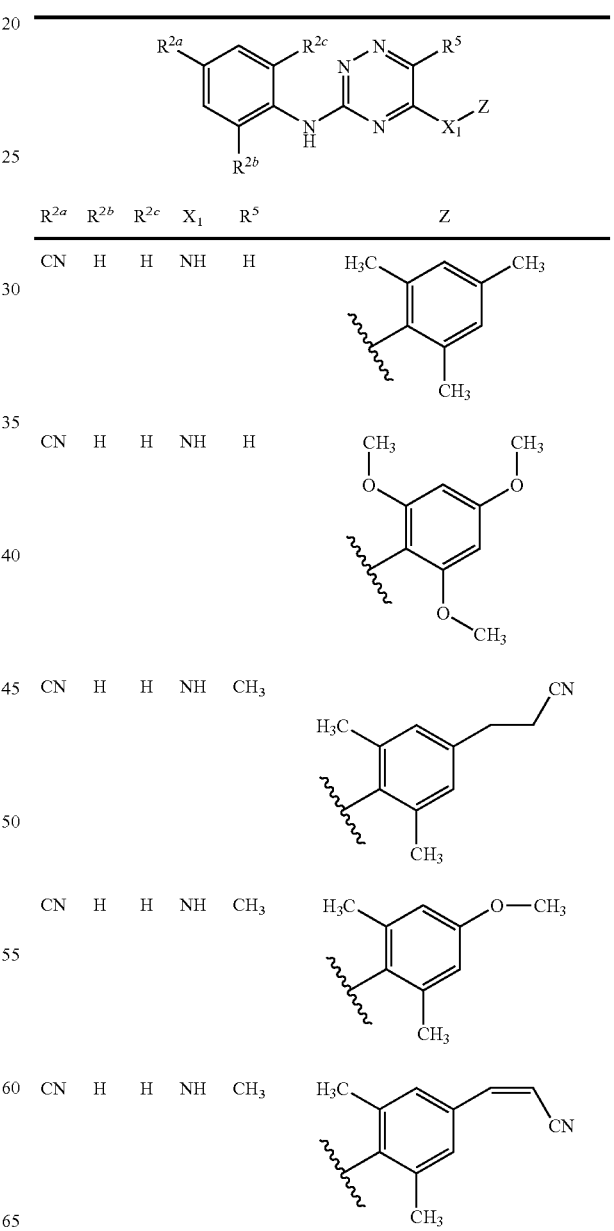

-continued

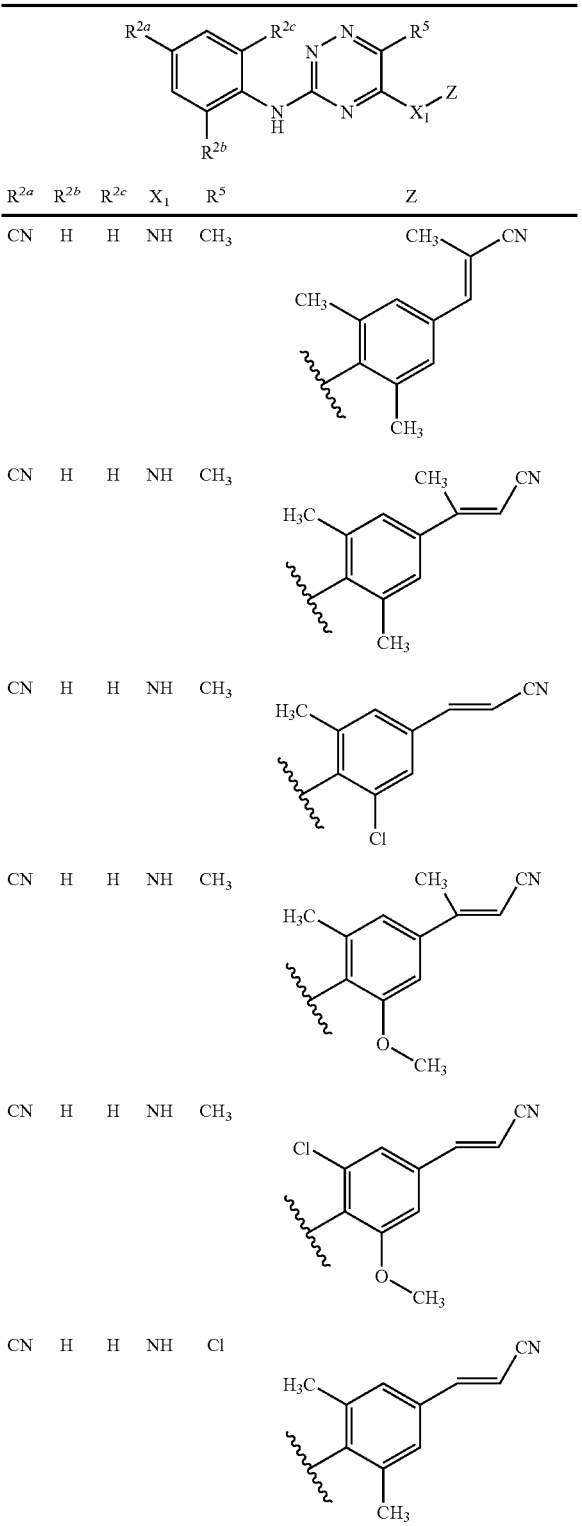

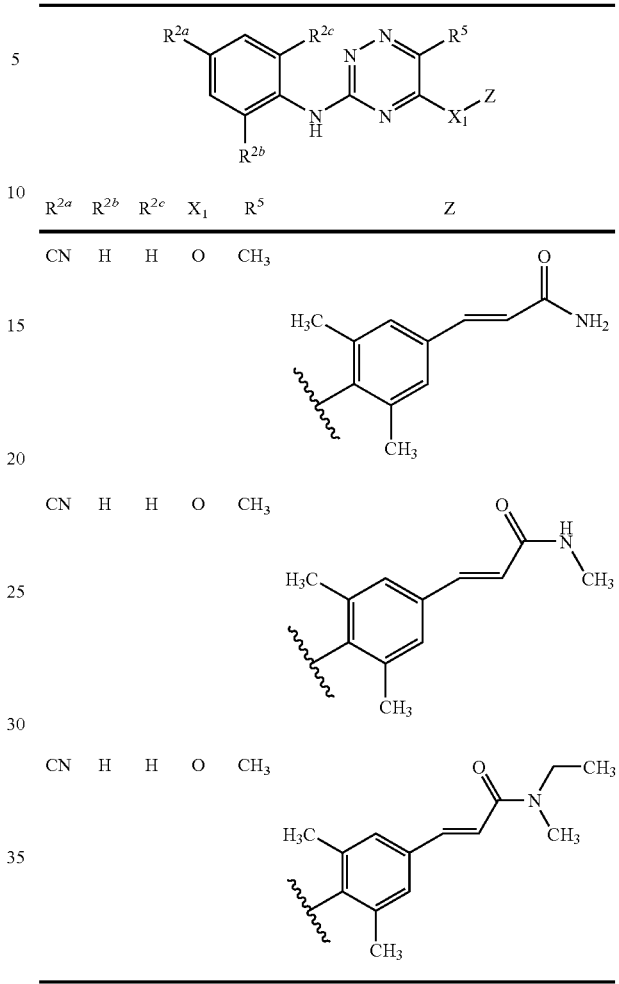

a N-oxide, a pharmaceutically acceptable acid or base addition salt or a stereochemically isomeric form thereof.

16. A method for the treatment of HIV (Human Immunodeficiency Virus) infection, comprising administering to a subject in need thereof a medicament that comprises a therapeutically effective amount of a compound of claim 1.

17. The method of claim 16, wherein the HIV (Human Immunodeficiency Virus) infection comprises (multi)drug resistant HIV infection.

18. A pharmaceutical composition comprising a pharmaceutically acceptable carrier and as active ingredient a therapeutically effective amount of a compound as claimed in claim 1.

19. A process for preparing a pharmaceutical composition comprising intimately mixing a therapeutically effective amount of a compound as claimed in claim 1 with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,585,861 B2 | Page 1 of 1 |
| APPLICATION NO. | : 10/544584 | |
| DATED | : September 8, 2009 | |
| INVENTOR(S) | : Lewi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 98 days.

Signed and Sealed this

Fourteenth Day of September, 2010

David J. Kappos
*Director of the United States Patent and Trademark Office*